(12) United States Patent
Durin et al.

(10) Patent No.: US 9,108,194 B2
(45) Date of Patent: Aug. 18, 2015

(54) METHOD AND APPARATUS FOR FRAGMENTING NUCLEIC ACIDS

(75) Inventors: Guillaume Durin, Boston, MA (US); James A. Laugharn, Jr., Winchester, MA (US)

(73) Assignee: Covaris, Inc., Woburn, MA (US)

( * ) Notice: Subject to any disclaimer, the term of this patent is extended or adjusted under 35 U.S.C. 154(b) by 859 days.

(21) Appl. No.: 13/242,665

(22) Filed: Sep. 23, 2011

(65) Prior Publication Data

US 2012/0077283 A1     Mar. 29, 2012

Related U.S. Application Data

(60) Provisional application No. 61/386,392, filed on Sep. 24, 2010.

(51) Int. Cl.
*G01N 1/28* (2006.01)
*B01L 3/00* (2006.01)
*C12N 15/10* (2006.01)
*C12Q 1/68* (2006.01)

(52) U.S. Cl.
CPC ............ *B01L 3/50215* (2013.01); *C12N 15/10* (2013.01); *C12Q 1/6806* (2013.01); *G01N 1/28* (2013.01); *B01L 3/50255* (2013.01); *B01L 2200/0631* (2013.01); *B01L 2200/0663* (2013.01); *B01L 2200/141* (2013.01); *B01L 2300/042* (2013.01); *B01L 2300/0681* (2013.01); *B01L 2300/0838* (2013.01); *B01L 2300/0841* (2013.01); *B01L 2300/0854* (2013.01); *B01L 2400/0409* (2013.01); *B01L 2400/086* (2013.01); *Y10T 436/25* (2015.01)

(58) Field of Classification Search
CPC ............ B01L 3/50215; B01L 3/50255; B01L 2200/0631; B01L 2200/0663; B01L 2200/141; B01L 2300/042; B01L 2300/0681; B01L 2300/0838; B01L 2300/0841; B01L 2300/0854; B01L 2400/0409; B01L 2400/086; C12Q 1/6806; C12N 15/10; G01N 1/28; G01N 1/286; G01N 1/2873
See application file for complete search history.

(56) References Cited

U.S. PATENT DOCUMENTS

| | | |
|---|---|---|
| 5,610,010 A | 3/1997 | Surzycki et al. |
| 2006/0057581 A1 | 3/2006 | Karlsen et al. |
| 2006/0133957 A1 | 6/2006 | Knapp et al. |
| 2009/0233814 A1 | 9/2009 | Bashkirov et al. |

OTHER PUBLICATIONS

Bowman et al. "Hydrodynamic Shear Breakage of DNA" *Biopolymers*, vol. 11, pp. 2601-2624 (1972).

(Continued)

*Primary Examiner* — Christopher A Hixson
(74) *Attorney, Agent, or Firm* — Wolf, Greenfield & Sacks, P.C.

(57) ABSTRACT

Systems and methods include processing devices used to fragment nucleic acids to average nucleic acid sizes ranging from between about 5 kbp and about 20 kbp. A processing device may include an inlet portion and a channel upstream from a shearing region arranged so that a relatively constant pressure is established and maintained (e.g., a pressure that changes by less than about 40%) at an entrance of the shearing region during a majority of sample flow through the shearing region. In some embodiments, after forcing the sample through the shearing region once, the processing device may be taken out of the centrifuge, inverted and placed back into the centrifuge so that the sample is forced through the shearing region again.

31 Claims, 24 Drawing Sheets

(56) References Cited

OTHER PUBLICATIONS

Oefner et al. "Efficient random subcloning of DNA sheared in a recirculating point-sink flow system" *Nucleic Acids Research*, vol. 24, pp. 3879-3886 (1996).

Thorstenson et al., "An Automated Hydrodynamic Process for Controlled, Unbiased DNA Shearing" *Genome Research*, vol. 8, pp. 848-855 (1998).

Joneja et al., "A device for automated hydrodynamic shearing of genomic DNA" *BioTechniques*, vol. 46, pp. 553-556 (2009).

International Search Report and Written Opinion from International Application No. PCT/US2011/052959 mailed Apr. 17, 2012.

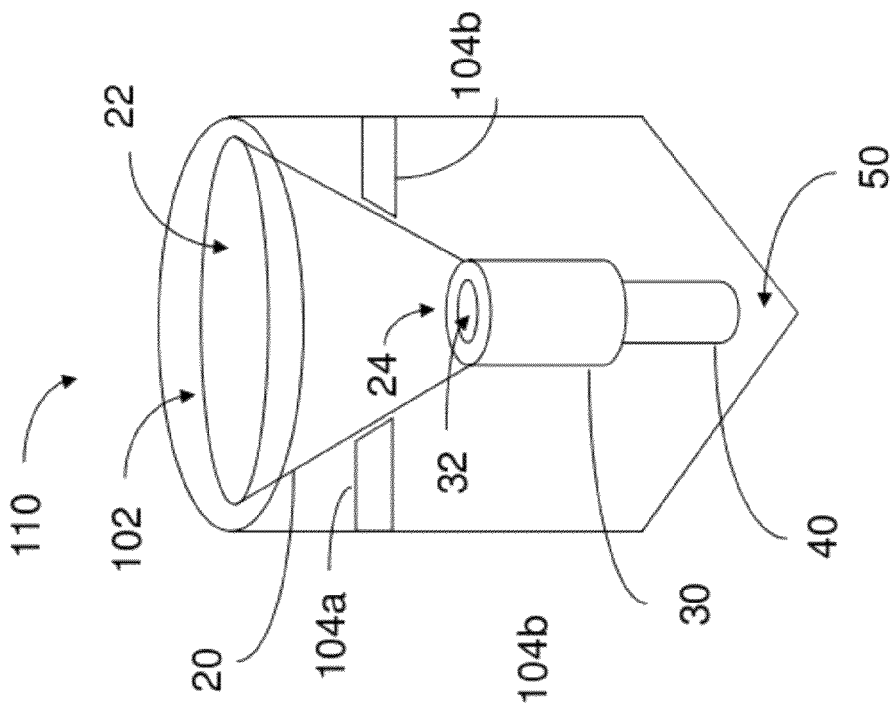
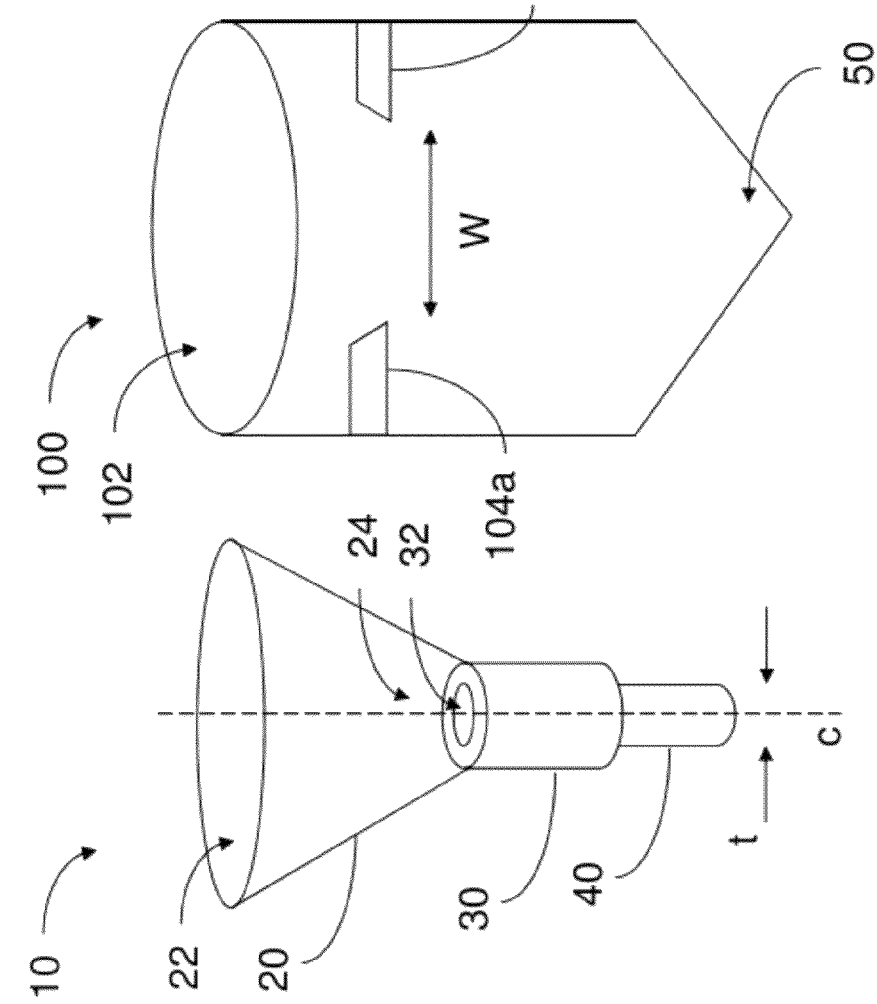

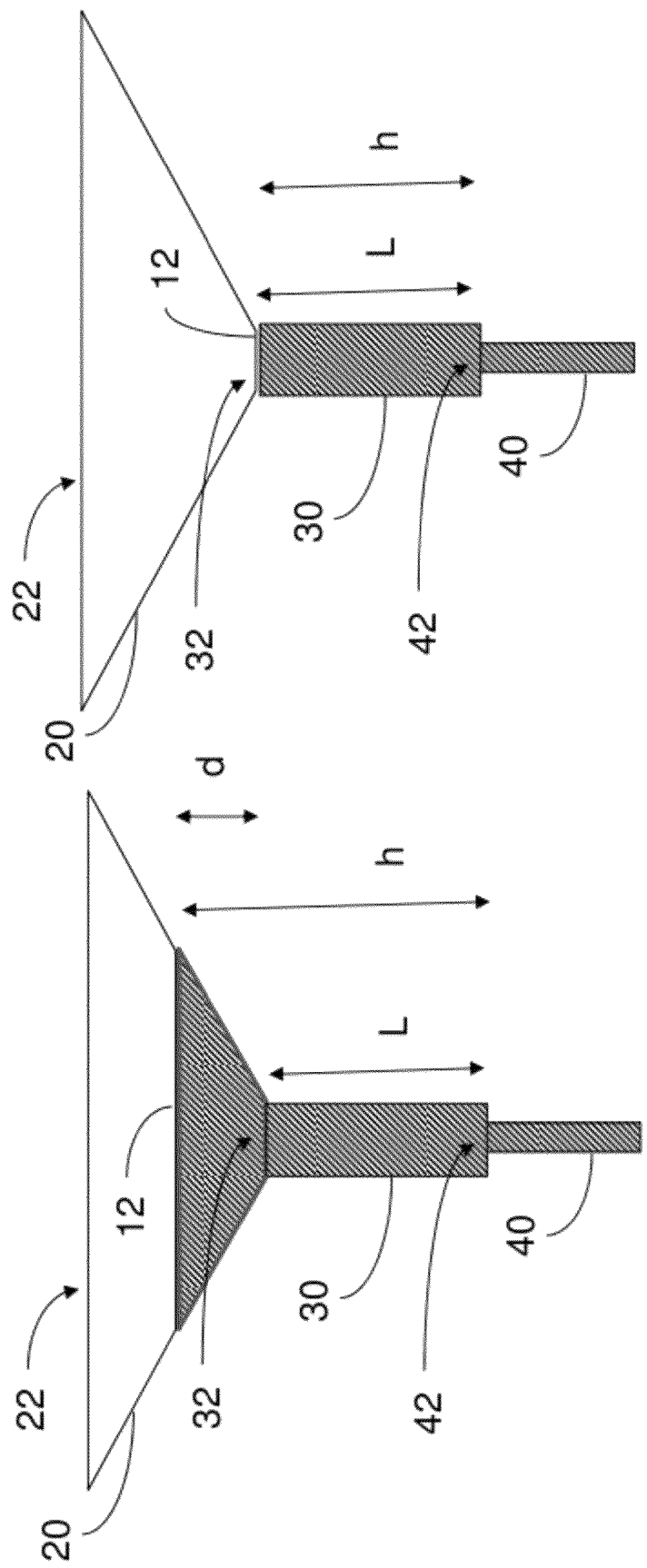

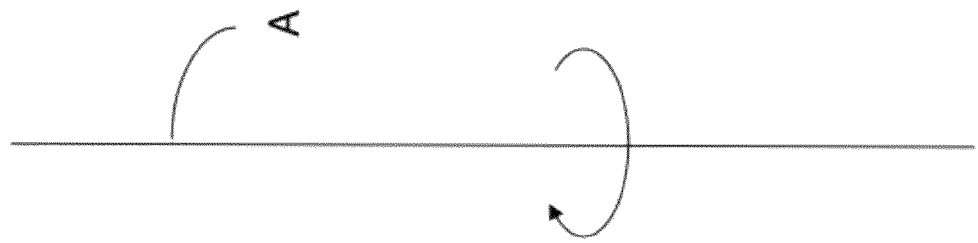
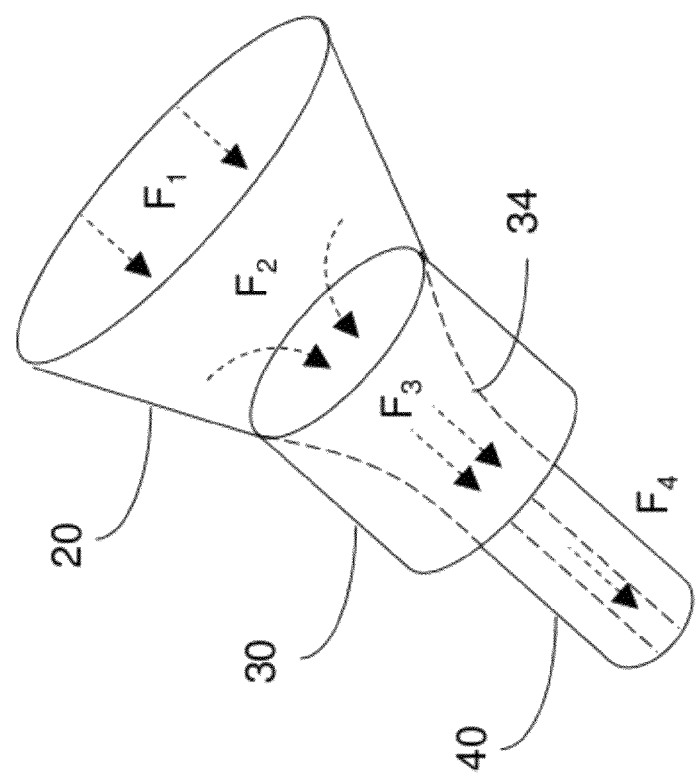
Fig. 4C

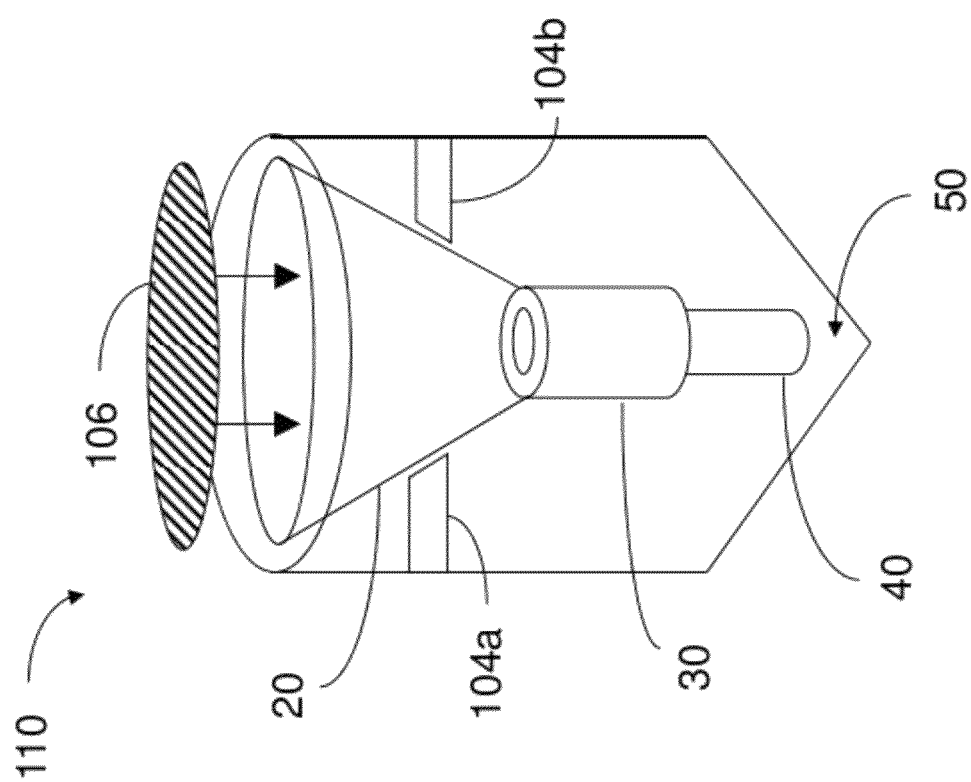

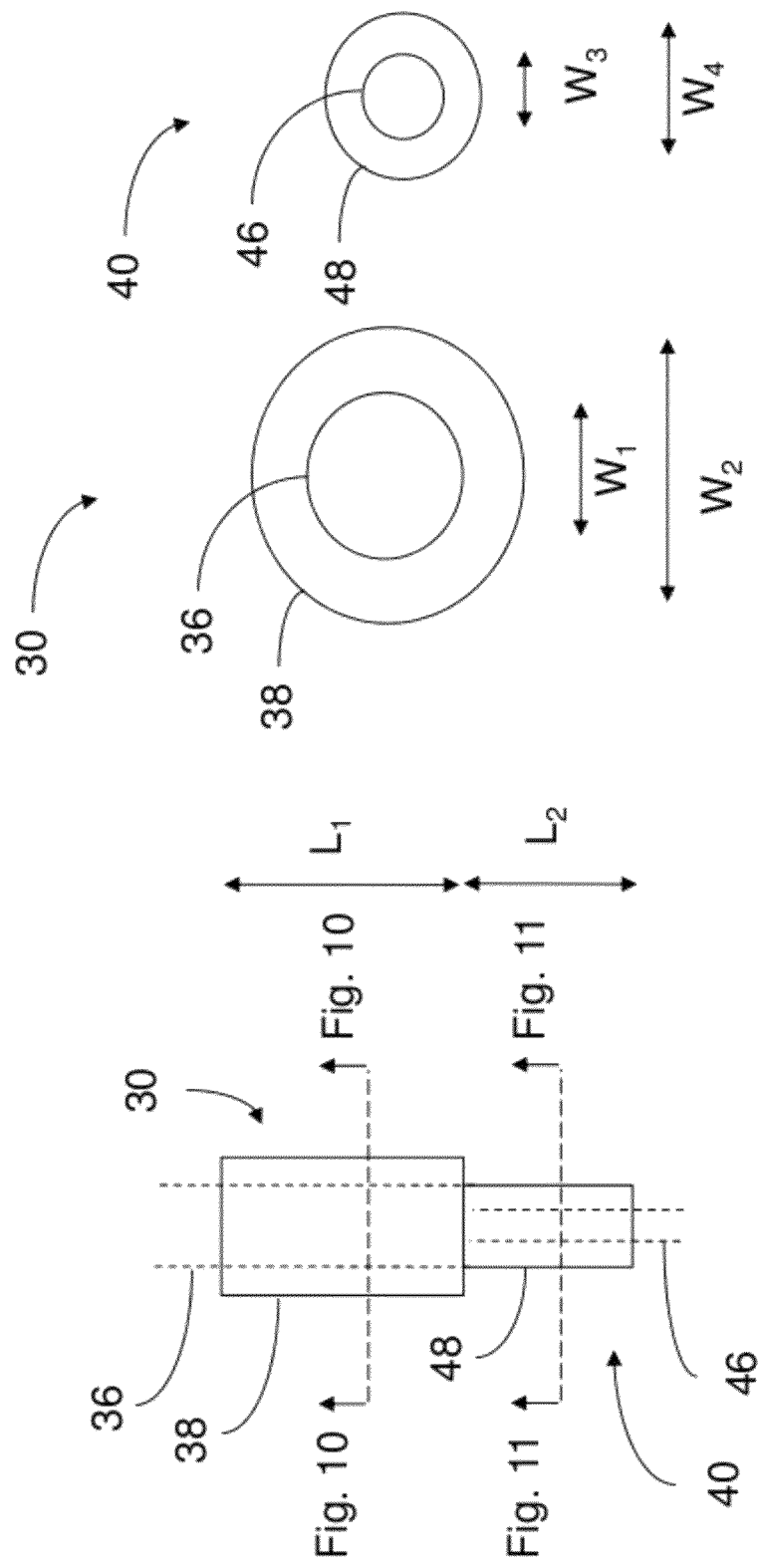

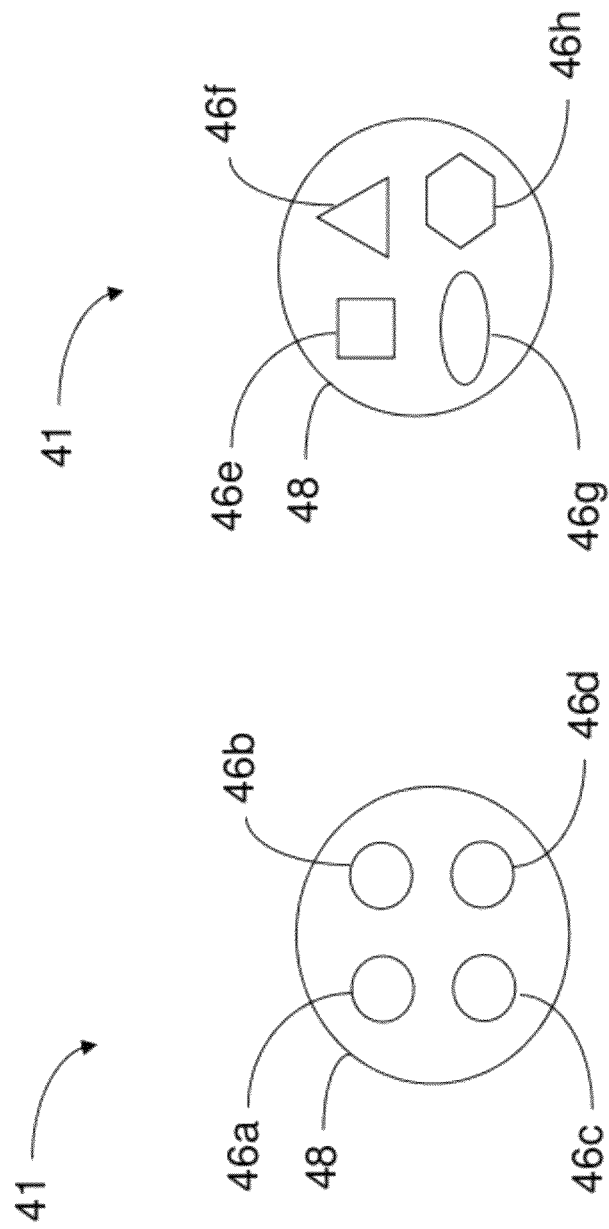

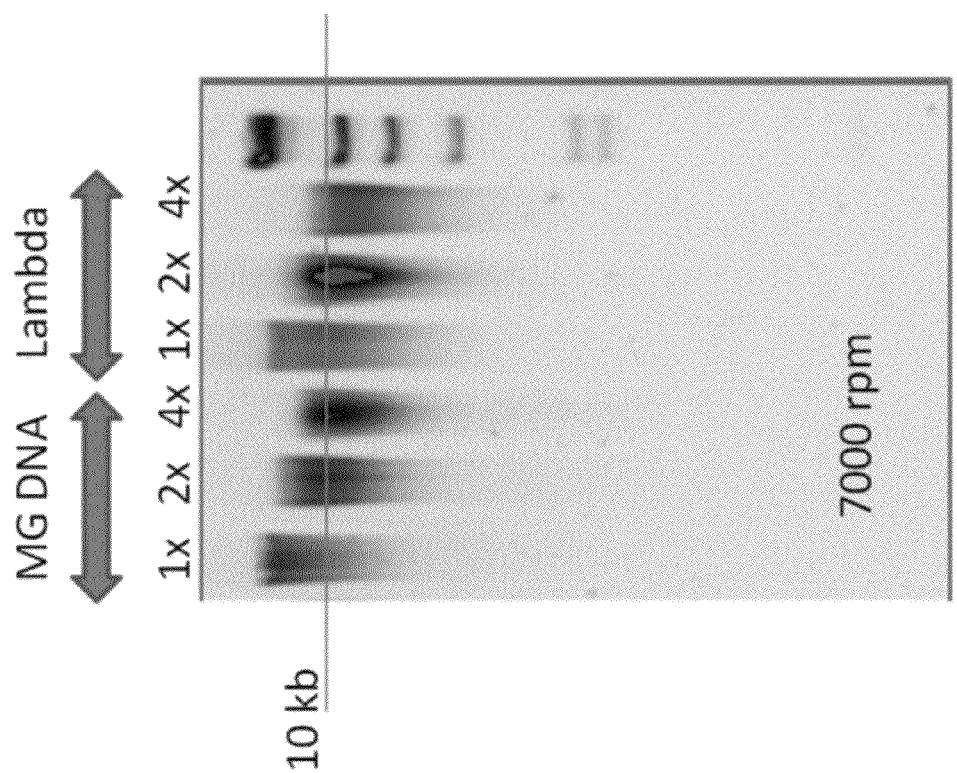

METHOD AND APPARATUS FOR FRAGMENTING NUCLEIC ACIDS

RELATED APPLICATIONS

This application claims the benefit of U.S. Provisional Application No. 61/386,392, filed Sep. 24, 2010, which is hereby incorporated by reference in its entirety.

BACKGROUND

1. Field of Invention

Aspects described herein relate to processing devices and methods of fragmenting materials such as nucleic acids. In some instances, processing devices may include a shearing region for fragmenting nucleic acids or other macromolecules in a sample upon suitable flow of the sample through the shearing region.

2. Related Art

Pumping a liquid solution into and through a small hole or capillary has been known to create strong velocity gradients in the solution. For solutions that contain DNA, such velocity gradients result in shearing forces that fragment DNA within the solution. A number of applications employ a pump to push and pull solutions having DNA through a small hole; however, such implementations can give rise to a number of issues. Existing systems that utilize pumping methods to push and pull liquid samples of DNA through small capillary holes can not only be expensive, but are highly susceptible to loss of DNA samples as well as cross contamination. Further, pumping a DNA sample to travel back and forth through a small hole can also be a slow and involved process.

For example, in some systems, a DNA solution is pushed from an inlet into a shearing orifice with a syringe where the solution is repeatedly pushed and pulled within the shearing orifice approximately 20 times. This process can take up to 20 minutes and is performed only on a single liquid solution of DNA at a time. Further, use of a syringe to push and pull a DNA solution within a shearing orifice gives rise to void volumes where a portion of the original solution is lost. Clogging of the orifice is also known to occur, resulting in leakages due to pressure in the flow tubing which can also lead to certain amounts of lost solution. Because cross contamination in shearing systems when samples are used in sequence presents an issue, the systems will often require washing steps which can not only be time consuming, but does not ensure that contamination will be prevented. Existing systems that cause movement of a sample of DNA through a shearing orifice are unable to regulate the pressure and flow rate through the system (e.g., establishing and maintaining a pressure at the entrance region to the shearing orifice), leading to undesirable results.

SUMMARY

The inventors have appreciated that prior shearing arrangements, such as that described in U.S. Patent Publication 2006/0133957, may experience relatively poor performance at least in part because appropriate pressures and/or flow rates of the sample fluid are not established at the shearing regions. That is, the inventors have found that shearing activity in an orifice depends at least in part on the pressure of the fluid at the orifice and the flow rate of the fluid, as well as other parameters, such as the size of the shearing orifice. Insufficient and/or variable pressures and/or flow rates at the shearing orifice have been found to result in poor shearing performance, e.g., inconsistent shearing of nucleic acid molecules, such as DNA, RNA, etc., that results in nucleic acid fragments having a size larger than desired or not having a desirable distribution. Inefficient shearing can complicate a shearing process since, for conventional shearing arrangements, incompletely sheared material must be passed through a shearing orifice several times, e.g., up to 10-20 times, in an effort to provide the desired result.

Aspects of the invention provide for methods and devices for shearing molecules, such as nucleic acids (e.g., DNA, RNA), that operate to establish and maintain appropriate pressures, flow rates and/or other parameters at the shearing orifice (e.g., at the entrance) so as to provide efficient shearing of the molecules. For example, some embodiments in accordance with aspects of the invention provide for shearing of nucleic acid molecules (e.g., DNA, RNA) having an initial size ranging between about 40 kbp and genomic sized nucleic acids (e.g., several Mbp, up to 1 Gbp in size) so that the resulting nucleic acid fragments have a size of about 5 to 20 kbp, in some cases, from a single pass through the shearing device. Shearing of the nucleic acid molecules may be performed by placing a shearing device containing appropriate sample material in a centrifuge and subsequently spinning the device in the centrifuge. The forces created by the centrifuge may provide the driving force to move the sample material through one or more shearing regions of the device. In some embodiments, the shearing device may include two or more shearing regions, e.g., to provide for an end product having sheared fragments with a uniform size, such as a finished sample having 90% or more of the sheared fragments having a size of under 10 kbp (e.g., about 5 kbp).

In some embodiments, the pressure at the entrance of the shearing region in a processing device may be established and maintained to be relatively constant during flow of a majority of the sample through the shearing region, for example, as a result of the structure of an inlet and a channel of the processing device. In some cases, the pressure at the entrance of the shearing region may be maintained to within about 40% of an initial pressure during flow of the majority of the sample through the shearing region. In some embodiments, a cross-sectional area of the inlet may be substantially greater than a cross-sectional area of the channel. In some embodiments, a volume of the inlet may be substantially greater than the volume of the channel. The larger cross-sectional area and/or volume of the inlet in comparison to the channel may permit the sample to flow through the shearing orifice with relatively little change in surface level height in the inlet over the shearing orifice. This relatively small change in surface level height may help to maintain a relatively constant head pressure over the shearing orifice, helping to improve shearing action.

In some embodiments, shearing of nucleic acids introduced into a shearing device may be performed more than once by causing the sample material having nucleic acids to move through a shearing region more than once. For example, a centrifuge may be used as an actuator to cause sample material to flow through the shearing region. The shearing device may subsequently be removed from the centrifuge, inverted and placed back into the centrifuge in the inverted configuration. The shearing device may be subject to centrifugal forces once again, causing the sample material to move back through the shearing region, thereby applying further shearing forces to the sample material. Accordingly, suitable shearing devices may be processed in a centrifuge, be subsequently inverted and then processed in the centrifuge again. Such a processing scheme may be employed as many times as desired.

Accordingly, aspects of the invention also relate to processing devices and methods used to fragment nucleic acids and/ or other materials to desirable size ranges and distributions of nucleic acid size. Processing devices include an inlet for receiving a sample that contains nucleic acids and a shearing region for fragmenting the nucleic acids in the sample upon suitable flow of the sample from the inlet through the shearing region. The shearing region has a geometry such that when a sample with a concentration of nucleic acid flows from the inlet and through the shearing region at an appropriate rate and/or pressure, a shearing force is applied to the sample to break apart bonds between nucleic acids. In some embodiments, the inlet may have a channel in fluid communication with a shearing orifice of the shearing region. The channel may be arranged so as to provide a generally constant or other desired flow rate or pressure of the sample at the orifice. For example, the channel may have a suitable funnel-like shape that serves to direct the sample fluid to the shearing region while maintaining a relatively constant head height over the shearing region. Portions of the inlet above the channel may be significantly larger in size than the channel, such as in cross-sectional area, so that the head height of the sample above the orifice may be maintained for a relatively wide range of sample volumes. Processing devices also include a collection portion that receives fragmented nucleic acids from the shearing region.

To induce flow of a sample containing nucleic acids from an inlet through a shearing region and into a collection portion, one or more processing devices may be coupled to a flow actuator that produces a force causing the sample to flow through shearing regions of the processing device at a suitable rate. In some embodiments, the flow actuator generates the force causing the sample to flow through the processing device without contact of the sample with a pump. For example, the flow actuator may be a centrifuge or an air (or other gas) pump that creates a pressure in the inlet that forces the sample to flow through the shearing region. Accordingly, when the flow actuator is a centrifuge, inlet, shearing and collection portions of processing devices are constructed and arranged to be placed within and for use in a centrifuge.

In accordance with another aspect of the invention, systems and methods for fragmenting nucleic acids in a sample are described where the entire volume of the sample is caused to flow through a shearing region. For example, by appropriately arranging a processing device for use in the centrifuge, an entire volume of sample provided to the inlet of the processing device may be forced through the shearing region and into a collection region. Accordingly, very little or no loss of sample may occur upon completion of fragmenting the nucleic acids in the sample. This is in contrast to some shearing arrangements in which a sample is caused to flow through a shearing orifice by operation of a syringe pump. In such devices, portions of the sample are trapped in "dead spots" of the syringe pump and/or in the shearing region because the syringe mechanism is simply incapable of causing the entire sample to move out of the syringe and through the shearing region. In another aspect, nucleic acids in a sample may be processed to a desired average nucleic acid size in less time than what would be the required processing time for existing shearing arrangements. For example, a sample containing nucleic acids with an initial average nucleic acid size may be fragmented to a final average nucleic acid size that is less than or equal to half of the initial average nucleic acid size (e.g., from 50 kbp down to 5-20 kbp) in less than 1 minute, or even in less than 30 seconds. In some embodiments, a sample with nucleic acids that flows only once through the shearing region of a processing device may be sheared such that a final average nucleic acid size of nucleic acids is less than or equal to half of the initial average nucleic acid size of the sample.

Other aspects of the invention relate to geometry of processing devices, e.g., a geometry of the device at or near the shearing region. In some embodiments, a shearing region of a processing device includes an entrance portion having a wall (e.g., inner or outer wall) with an angle that is substantially perpendicular to a direction of flow of the sample through the shearing region. In some embodiments, a portion of an inlet of a processing device is funnel-shaped so as to maintain desired pressures, flow rates or other parameters of the sample. For example, the inlet of the processing device may have an entrance region having a cross sectional area that is larger than a cross sectional area of a distal end region of the inlet, where the distal end of the inlet leads toward the shearing region of the device. A distal end of the inlet may include a channel that leads toward a shearing orifice. The channel may provide a conduit arranged so that sample flow through the orifice remains within a suitable range of flow rates for a majority of sample flow through the orifice. In some embodiments, an inlet and channel may maintain a constant sample height over the shearing orifice during a majority of sample flow through the processing device, giving rise to a desired pressure that is relatively constant at a shearing orifice that facilitates a suitable flow rate through the shearing orifice.

In an illustrative embodiment, a processing device for fragmenting nucleic acids contained within a sample is provided. The device includes an inlet portion for receiving the sample containing nucleic acids; a channel having a channel volume in fluid communication with the inlet portion; a shearing region in fluid communication with the channel and adapted to fragment the nucleic acids in the sample upon flow of the sample through the shearing region, wherein the inlet portion and the channel are constructed and arranged to maintain a relatively constant pressure at an entrance of the shearing region during flow of a majority of a sample through the shearing region where the sample has a volume that is at least 2 times the channel volume; and a collection portion in fluid communication with the shearing region and for receiving the sample containing the fragmented nucleic acids from the shearing region, wherein the inlet portion, the channel, the shearing region and the collection portion are constructed and arranged for use with a flow actuator to move the sample containing nucleic acids from the inlet portion through the channel and the shearing region into the collection portion. In some embodiments, the inlet portion and channel may be arranged to maintain a relatively constant pressure at the entrance to the shearing region during flow of a majority of a sample through the shearing region where the sample has a volume that is at least 4, 5, 6, 8, 10 or more times the channel volume.

In another illustrative embodiment, a processing device for fragmenting nucleic acids contained within a sample is provided. The device includes an inlet portion for receiving the sample containing nucleic acids; a shearing region in fluid communication with the inlet portion and adapted to fragment the nucleic acids in the sample upon flow of the sample through the shearing region; and a collection portion in fluid communication with the shearing region and for receiving the sample containing the fragmented nucleic acids from the shearing region, wherein the inlet portion, the shearing region and the collection portion are constructed and arranged for use in a centrifuge in either a first orientation or in a second orientation that is inverted with respect to the first orientation.

In a further illustrative embodiment, a method of fragmenting nucleic acids contained within a sample is provided. The method includes providing the sample containing nucleic acids to an inlet portion of at least one processing device; forcing the sample to flow through a shearing region of the at least one processing device in a first direction; applying a shearing force to nucleic acids in the sample to fragment the nucleic acids as the sample flows in the shearing region; maintaining a relatively constant pressure at an entrance to the shearing region during a majority of a processing time where the shearing force is applied to nucleic acids; and collecting the sample containing fragmented nucleic acids in the collection region.

In yet another illustrative embodiment, a method of fragmenting nucleic acids contained within a sample is provided. The method includes providing the sample containing nucleic acids to an inlet portion of at least one processing device; forcing the sample to flow through a shearing region of the at least one processing device from force generated by a centrifuge; applying a shearing force to nucleic acids in the sample to fragment the nucleic acids as the sample flows in the shearing region to an average nucleic acid size of less than about 10 kbp; and collecting the sample containing fragmented nucleic acids in the collection region.

In one illustrative embodiment, a processing device for fragmenting nucleic acids is provided. The device includes an inlet portion for receiving a sample containing nucleic acids; a shearing region in fluid communication with the inlet portion and adapted to fragment the nucleic acids in the sample upon flow of the sample from the inlet portion through the shearing region; and a collection portion in fluid communication with the shearing region and for receiving the sample containing the fragmented nucleic acids from the shearing region. The inlet portion, the shearing region and the collection portion are constructed and arranged for use in a centrifuge to move the sample containing nucleic acids from the inlet portion through the shearing region.

In another illustrative embodiment, a system for shearing nucleic acids to produce fragmented nucleic acids is provided. The system includes at least one processing device and a flow actuator. The at least one processing device includes an inlet portion for receiving a sample containing nucleic acids, a shearing region adapted to fragment the nucleic acids in the sample upon flow of the sample through the shearing region, and a collection portion for collecting the sample containing fragmented nucleic acids from the shearing region. The flow actuator is coupled to the at least one processing device and is adapted to produce a force that causes flow of the sample from the inlet portion through the shearing region into the collection portion of the at least one processing device without contact of the sample with a pump.

In a different illustrative embodiment, a method of fragmenting nucleic acids is provided. The method includes providing a sample containing nucleic acids to an inlet portion of at least one processing device; forcing the sample to flow through a shearing region of the at least one processing device without contacting the sample with a pump; applying a shearing force to nucleic acids in the sample to fragment the nucleic acids as the sample flows in the shearing region; and collecting the sample containing fragmented nucleic acids in the collection region.

In yet another illustrative embodiment, a system for shearing nucleic acids to produce nucleic acid fragments having a desired average size is provided. The system includes at least one processing device and a flow actuator. The at least one processing device includes an inlet portion for receiving a sample containing nucleic acids and having a sample volume, a shearing region adapted to fragment the nucleic acids in the sample upon flow of the sample through the shearing region, and a collection portion for collecting the sample containing fragmented nucleic acids. The flow actuator is coupled to the at least one processing device and is adapted to induce flow of the sample from the inlet portion through the shearing region into the collection portion of the at least one processing device such that the entire sample volume flows from the inlet portion and through the shearing region to the collection portion.

In another illustrative embodiment, a method of fragmenting nucleic acids is provided. The method includes providing a sample containing nucleic acids and having a sample volume to the inlet portion of the at least one processing device; forcing the entire sample volume to flow through the shearing region of the at least one processing device; applying a shearing force to nucleic acids in the sample to fragment the nucleic acids as the sample flows in the shearing region; and collecting the sample containing fragmented nucleic acids in the collection region.

In yet a different illustrative embodiment, a method of fragmenting nucleic acids is provided. The method includes providing a sample containing nucleic acids having an initial average nucleic acid size to an inlet portion of at least one processing device; and causing the sample to flow through a shearing region of the at least one processing device to fragment nucleic acids in the sample within 1 minute or less such that a final average nucleic acid size of the sample after flow through the shearing region is less than or equal to half of the initial average nucleic acid size.

In an illustrative embodiment, a processing device for fragmenting nucleic acids is provided. The device includes an inlet portion for receiving a sample containing nucleic acids; a shearing region having an entrance portion having an inner wall that forms an angle perpendicular to a direction of flow of the sample through the shearing region so as to fragment the nucleic acids in the sample upon flow of the sample from the inlet portion into the entrance portion of the shearing region; and a collection portion for receiving the sample containing the fragmented nucleic acids from the shearing region.

In a different illustrative embodiment, a method of fragmenting nucleic acids is provided. The method includes providing a sample containing nucleic acids having an initial average nucleic acid size to an inlet portion of at least one processing device; and causing the sample to flow once through a shearing region of the at least one processing device to fragment nucleic acids in the sample such that a final average nucleic acid size of the sample after flow through the shearing region is less than or equal to half of the initial average nucleic acid size.

In another illustrative embodiment, a processing device for fragmenting nucleic acids is provided. The device includes a funnel-shaped inlet portion for receiving a sample containing nucleic acids, the inlet portion having an entrance region and a distal end region, wherein a cross sectional area defined at the entrance region of the inlet portion is greater than a cross sectional area defined at the distal end region of the inlet portion; a shearing region disposed adjacent the distal end region of the inlet portion, the shearing region adapted to fragment the nucleic acids in the sample upon flow of the sample from the inlet portion through the shearing region; and a collection portion for receiving the sample containing the fragmented nucleic acids from the shearing region.

The foregoing is a non-limiting summary of the invention, which is defined by the attached claims. Other aspects, embodiments, features will become apparent from the following description.

BRIEF DESCRIPTION OF THE DRAWINGS

The accompanying drawings are not intended to be drawn to scale. In the drawings, each identical or nearly identical component that is illustrated in various figures is represented by a like descriptor. For purposes of clarity, not every component may be labeled in every drawing.

The advantages and features of this invention will be more clearly appreciated from the following detailed description, when taken in conjunction with the accompanying drawings.

FIG. 1A shows an illustrative embodiment of inner portions of a processing device for fragmenting nucleic acids;

FIG. 1B depicts an illustrative embodiment of an outer portion of a processing device;

FIG. 2 shows an illustrative embodiment of a processing device for fragmenting nucleic acids;

FIG. 3A depicts a processing device in accordance with various embodiments;

FIG. 3B illustrates the processing device of FIG. 3A;

FIG. 4C illustrates the embodiment of the processing device according to FIG. 4A disposed at an angle and depicting directions of flow of sample through the device;

FIG. 8 depicts a different illustrative embodiment of a processing device suitable for fragmenting nucleic acids;

FIG. 9 shows a side view of an embodiment of a shearing region including orifices of a processing device;

FIG. 10 depicts a cross sectional view of the shearing orifice according to the line indicated in FIG. 9;

FIG. 11 depicts another cross sectional view of the shearing orifice according to the line indicated in FIG. 9;

FIG. 12 illustrates a cross sectional view of a plurality of shearing orifices according an embodiment;

FIG. 13 illustrates a cross sectional view of another plurality of shearing orifices according an embodiment;

FIG. 27 depicts results from a different processing example in accordance with an embodiment.

DETAILED DESCRIPTION

Figure 4A:
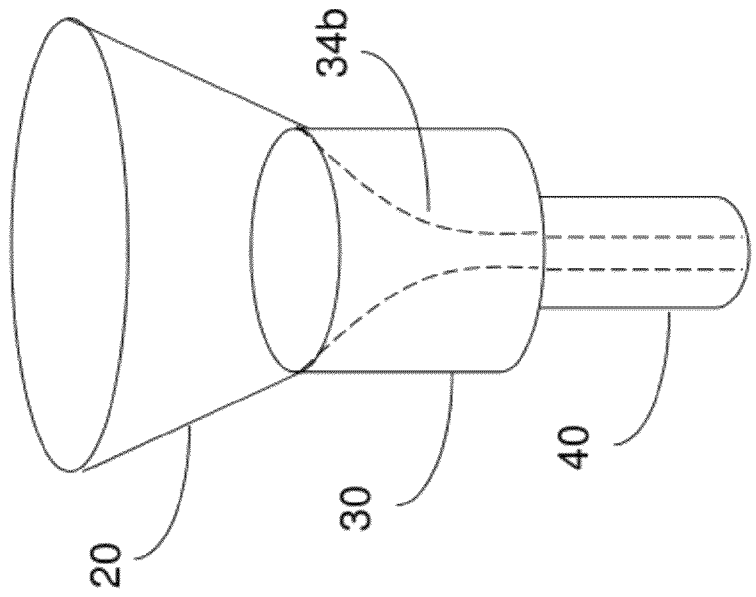
FIG. 4A illustrates an embodiment of a processing device for fragmenting nucleic acids.

It should be understood that illustrative embodiments are described in accordance with aspects discussed herein, with some reference to the figures. The embodiments described are not necessarily intended to show all aspects of the invention, but rather are used to describe a few illustrative embodiments. Thus, aspects discussed herein are not intended to be construed narrowly in view of the illustrative embodiments. In addition, it should be understood that aspects described may be used alone or in any suitable combination with other aspects also described.

Systems and methods are described that include processing devices used to fragment and recover nucleic acids (e.g., DNA, RNA) having a desired range of average nucleic acid sizes. For example, solutions containing relatively large-sized nucleic acids (e.g., nucleic acids having sizes starting at about 40-50 kbp and ranging up to nucleic acids that are genomic in size, several Mbp, 1 Gbp, etc.) can be fragmented into medium-sized nucleic acids ranging from about 5 kbp to about 20 kbp (e.g., less than about 20 kbp, less than about 10 kbp). In some cases, nucleic acids can be fragmented down to average sizes below 5 kbp. Such a result may occur without the presence of a number of shortcomings that may typically arise in conventional systems that are used for nucleic acid fragmentation. In some embodiments, a sample (e.g., a liquid solution, emulsion, suspension, etc.) containing nucleic acids is introduced into an inlet portion of a processing device. A force is applied to the sample, causing the sample to flow from the inlet portion through a shearing region of the device having a geometry that is suitable to apply shear forces to the sample to fragment the nucleic acids in a desirable manner.

In some embodiments, once the sample has flowed through the shearing region, nucleic acids are fragmented to a final average nucleic acid size (e.g., 5-20 kbp, 1-10 kbp, 5-10 kbp) that is about less than or equal to half of an initial average nucleic acid size (e.g., 48-50 kbp) contained within the sample upon first having introduced the sample into the processing device. In some embodiments, the initial average nucleic acid size is substantial and may be on the order of several Mbp (e.g., nucleic acids that are genomic or chromosomal in size). In accordance with various embodiments, such large nucleic acids may also be suitably fragmented down to a desirable nucleic acid size. In some embodiments, a sample containing nucleic acids is subject to force generated by a centrifuge resulting in sample flow from an inlet through a shearing region of a processing device for inducing nucleic acid fragmentation.

Suitable samples may contain materials other than nucleic acids. In some embodiments, samples include cells where the cells are lysed when the sample flows through certain regions of the processing device, such as a shearing region. Cells in a sample may lyse when the sample flows through other portions of the processing device also, for example, during flow of sample from an inlet to a channel or flow from a channel to a collection portion. Samples may include other chemical or biological materials, such as proteins, lipids, synthetic polymers, emulsions, suspensions, or other suitable formulations including macromolecules.

In one aspect, samples of nucleic acids are processed from an initial average nucleic acid size to a final average nucleic acid size more efficiently than is possible with existing shearing equipment. In some embodiments, a force that moves the sample from the inlet portion through the shearing region to fragment nucleic acids in the sample is applied for less than 1 minute, or less than 30 seconds, and the sample having nucleic acids fragmented to a desired average size is retrieved. While it should be appreciated that flow through a processing device from an inlet through a shearing region may occur multiple times (e.g., through back and forth actuation or inversion of the processing device so that flow occurs back through the shearing region), in some cases, however, flow through the shearing region occurs only once. In instances where flow of a sample occurs from an inlet through a shearing region of a processing device only once through, desired average nucleic acid sizes and distributions, such as nucleic acid sizes that are less than or equal to half of an initial average nucleic acid size, may be recovered.

Not only are systems and methods described that provide for quick fragmentation of nucleic acids, aspects discussed provide for a process of nucleic acid fragmentation without sample loss. In some embodiments, the entire volume of a sample that is initially introduced into an inlet of a processing device flows through regions of the processing device and the entire volume having a desired average nucleic acid size is recovered at the end of the fragmentation process in a collection region.

An illustrative embodiment of a processing device 110 are depicted in FIGS. 1A-2. In this embodiment, the processing device 110 includes an inner portion 10, shown in FIG. 1A, and an outer portion 100, shown in FIG. 1B, where the inner portion 10 is arranged for placement in the outer portion 100 upon assembly of the processing device 110, shown in FIG. 2.

As depicted in the embodiment of FIG. 1A, an inner portion 10 of a processing device 110 includes an inlet and a shearing region. In this embodiment, the inlet includes an inlet portion 20 coupled to a channel 30 and the shearing region includes a shearing orifice 40 that is coupled to the channel 30. The inlet portion 20, the channel 30 and the shearing orifice 40 may be connected in a manner such that a sample may flow from the inlet portion through the channel and into the shearing orifice, without being confined in any particular region of the inlet portion. For example, as described later with respect to FIGS. 4A and 4B, the inlet portion 20 and the channel 30 may be arranged so that the chance that portions of the sample pool or otherwise are prevented from flow through the processing device is reduced. The inlet portion 20 has an entrance region 22 that is suitable to receive a sample containing nucleic acids, e.g., received via a pipette or other liquid handling device. In some embodiments, an inlet portion 20 is a pipette tip or a structure similar to a pipette tip.

In some embodiments, the channel 30 is arranged such that a desired pressure is created at the entrance of shearing orifice 40. Pressure at the entrance of shearing orifice 40 may be proportional to the height of the sample disposed within channel 30 over the shearing orifice 40. In some embodiments, portions of the device are dimensioned so the channel 30 remains full during a significant portion of the fragmentation process. Accordingly, the height of the sample in channel 30 and inlet portion 20 over the shearing orifice 40 remains relatively constant, i.e., the sample height does not change significantly (e.g., by less than 40%). By maintaining the height of the sample over the shearing orifice 40 to be relatively constant as the sample flows through the shearing orifice, the pressure established at the entrance of the shearing orifice 40 may also be made relatively constant. As a result, the pressure at the entrance to the shearing orifice may differ by only a slight amount when the inlet portion 20 and the channel 30 are completely filled with a sample, as compared to when only the channel 30 is filled with sample and the inlet portion 20 is empty.

FIGS. 3A and 3B illustrate the phenomenon described above where the processing device includes a sample 12. As shown in FIG. 3A, the height h of the sample 12 extends just beyond the length L of the channel 30 a distance d, where the distance d is much smaller than the length L of the channel 30. For example, the length L of the channel may be more than 2 times, more than 3 times, more than 5 times, or more than 10 times greater than the distance d or the height of the inlet portion itself. As it can be appreciated that the figures are not intended to be drawn to scale, the volume of the inlet portion 20 may be substantially greater than the volume of channel 30. Similarly, a cross-sectional area of the inlet portion, for example, at the entrance 22 as well as other regions, may be substantially greater than the cross-sectional area of the channel. Accordingly, as the sample moves through the processing device, the height h decreases slowly. Thus, while the channel 30 remains full of sample, the height h continues to be much greater than the distance d and, relative to the amount of sample moving through the channel, the height h remains relatively constant, i.e., the height does not vary by a significant amount.

In some embodiments, when the height h of the sample remains relatively constant as described herein, the height h changes by less than 50%, less than 40%, less than 30%, less than 20%, or less than 10% of the initial sample height prior to evacuation of the inlet portion 20. As the sample height h remains relatively constant, the pressure at the entrance 42 of the shearing region 40 also remains relatively constant. FIG. 3B illustrates an instance when a significant amount of the sample (e.g., a majority of the sample that had initially been placed in the inlet) has flowed through the shearing region and the inlet portion 20 is essentially emptied. As a result, the sample height h is about equal to the length L of the channel 30. Thus, because the cross-sectional area and/or the volume of the channel is much smaller than the cross-sectional area and/or volume of the inlet portion, the sample height h will remain substantially constant at least until the sample height equals the channel length L.

As alluded to above, in various embodiments, a cross-sectional area of the inlet portion (e.g., as an average of the cross-sectional area of the inlet over its height and/or near the entrance or at a distal region in the inlet portion near the channel inlet) may be substantially greater than the cross-sectional area of the channel. For example, a cross-sectional area of the inlet portion may be more than 5 times, more than 10 times, more than 20 times, more than 50 times, or more than 100 times greater than the cross-sectional area of the channel. In some embodiments, the volume of the inlet portion (e.g., a volume intended to receive sample) may be substantially greater than the volume of the channel. For example, the volume of the inlet portion may be more than 2 times, more than 5 times, more than 10 times, more than 20 times, more than 50 times, or more than 100 times greater than the volume enclosed by the channel. Such a structure may give rise to a sample height that decreases very slowly during a majority of sample flow through the shearing region, resulting in both a relatively constant sample height as well as a relatively constant pressure at the entrance to the shearing region. Considered another way, such a structure may result in the flow velocity at a surface of the sample in the inlet portion, or otherwise within the inlet portion, being substantially smaller than the flow velocity of the sample within the shearing region or the channel.

In some embodiments, the difference in pressure that arises at the entrance of the shearing orifice in the case of a filled channel and filled inlet portion, as compared to the case of a filled channel and empty inlet portion, is less than about 50%, less than about 40%, less than about 30%, less than about 25%, less than about 20%, or less than about 15%. In other embodiments, the pressure at the entrance of the shearing orifice in the case where only the channel is filled with sample may differ by less than about 50%, less than about 40%, less than about 30%, less than about 25%, less than about 20%, or less than about 15% of an initial pressure at the shearing orifice when the device holds a sample having a volume that is at least 2, 4, 5, 6, 8, 10 or more times the volume of the channel. In other embodiments, a ratio of a cross-sectional area of the inlet portion to the channel length may be minimized so that a pressure change at the shearing orifice inlet is minimized as sample is drawn from the inlet portion. In some cases, the inlet portion cross-sectional area to channel length ratio may be about 1.0 or more. Of course, features of inlet cross-sectional area to channel length ratio, pressure difference ratios based on different sample volume to channel volume ratios, inlet portion to channel cross-sectional area ratios, etc., may be combined together in any suitable way in a single embodiment. Accordingly, the pressure at the entrance of the shearing region may remain relatively constant during flow of a majority of the sample from the inlet through the shearing region.

A suitable pressure may be established and maintained to be relatively constant at the entrance region of a shearing orifice where the channel upstream to the shearing orifice is filled (i.e., including situations where the inlet portion is filled or empty). In some embodiments, when the channel leading to the shearing orifice is filled with sample material, the pressure at the entrance of the shearing orifice ranges between about 10 psi and about 150 psi, between about 15 psi and about 100 psi, between about 20 psi and about 50 psi, or between about 25 psi and about 40 psi. Other pressures at the entrance of the shearing orifice outside of these ranges are also possible.

To illustrate the ability for certain regions of devices described herein to exhibit only very small changes in pressure, consider an example processing device having a cylindrical inlet portion having a height of 3 mm, an inlet diameter of 9 mm and able to hold a volume of about 200 microliters; and a cylindrical channel that has a length of 10 mm, an opening diameter of 1.5 mm and able to hold a volume of about 17 microliters; where the inlet portion and channel are subject to a force generated by a centrifuge of 4500 g. In this example, when the inlet portion is empty and the channel is filled with sample, the pressure at the entrance of the shearing region is about 28 psi. However, when both the inlet portion and the channel are filled with sample, which corresponds to an increase in sample volume of 183 microliters, the pressure at the entrance of the shearing region only increases to 35 psi. Accordingly, such a minimal increase of 7 psi in pressure is considered negligible (i.e., the pressure remains relatively constant, varying by only about 25%) considering that the processing device is filled with the extra 183 microliters of sample. Accordingly, during operation, as 183 microliters of sample flows through the shearing region, the pressure at the entrance of the shearing region remains relatively constant, only changing from about 35 psi to about 28 psi. However, after the sample is emptied from the inlet portion, the pressure drops rapidly as the sample quickly flows through the channel and through the shearing region, but this pressure change is only experienced for less than about 17 microliters of sample—less than about 10% of the total sample volume. Thus, in this embodiment, the processing device is arranged to keep a pressure at the shearing region within about a 25% variation for a majority of the sample where the sample has a volume that is greater than about 12 times the volume of the channel. Also, the inlet portion cross-sectional area to channel length ratio in this example is about 6.4.

The inlet portion 20, on the other hand, may have a size, volume or other configuration that is significantly larger than the channel 30 so that the head height of the sample in the channel 30 remains relatively constant even as sample is drawn from the inlet portion 20. For example, inlet portion 20 may have a funnel-like shape with a larger size, e.g., cross-sectional area, at the entrance 22 (e.g., having an inner diameter approximately 10 mm or less) and a smaller size, e.g., cross-sectional area, near the channel 30. As described previously, the inlet portion 20 may therefore be arranged so that the height of the sample in the inlet portion 20 decreases slowly and/or varies relatively little during sample processing. For example, a height of the sample in the channel 30 may be much larger than that in the inlet portion 20, and the inlet portion 20 may, in turn, have a larger volume than the channel 30 so that as sample moves through the shearing region 40, the total height h of the sample over the orifice 40 (i.e., the height in the channel 30 and the inlet portion 20) changes relatively little as sample is drawn from the inlet portion 20. Accordingly, as discussed above, while the height of the sample in the inlet portion 20 slowly decreases during sample processing, the height of the sample disposed within the channel 30 may remain relatively constant, providing for a generally desired pressure and/or flow rate at the orifice 40. An outer diameter of the inlet portion of a processing device may be less than about 15 mm, less than about 11 mm, and/or such that the device may fit into a centrifuge. An inner diameter of the inlet portion may vary depending on location along the inlet portion, for example, near the entrance of the inlet portion contrasted with the region where the inlet portion is coupled with a channel. The inner diameter of the inlet portion may be less than 10 mm, or may range between about 9 mm and about 1 mm or may be less. In some embodiments, an inner diameter of an inlet portion is constructed so as to hold as much sample volume as possible while minimizing variations in pressure in the channel at the shearing region. In some embodiments, the volume of sample held within an inlet portion ranges between about 50 microliters and about 500 microliters.

The shearing orifice 40 may have any suitable arrangement, e.g., may be a jeweled structure formed of ruby, sapphire or other appropriate material. The shearing orifice may have a suitable internal orifice diameter, for example, a diameter of between about 10 microns and about 100 microns, between about 50 microns and about 100 microns, or between about 10 microns and about 50 microns. The shearing orifice may also have any suitable length, such as a length of between about 1 mm and about 50 mm, or between about 5 mm and about 20 mm. Other sizes or arrangements for the shearing orifice 40 are possible, however. In some cases, a shearing orifice may be a thin and stiff member, e.g., having an outer diameter of 1 mm or less, which can present a danger for when users handle the shearing orifice. In some embodiments (not expressly shown in the figures), a protective region such as a skirt portion may be provided around the shearing orifice to better protect users that may handle such devices.

In some embodiments, a shearing region incorporating an orifice includes a ruby disc and a glass capillary arranged in series and having a hole that runs through the middle of the disc along the cylindrical axis c. The ruby disc and/or the glass capillary may have any suitable outer thickness t, such as for example, an outer thickness of between about 50 microns and about 500 microns. For example, in an embodiment, the ruby disc has an outer thickness of about 250 microns and the glass capillary has an outer thickness of about 100 microns. In an embodiment, the hole that runs through the middle of the disc has a 30 micron diameter. The ruby disc and/or the glass capillary may have any suitable length, such as a length of between about 1 mm and about 50 mm. In an embodiment, the glass capillary is 5 to 20 mm in length. Referring back to FIG. 1A, an embodiment of an outer portion 100 of a processing device 110 is depicted and may be, for example, in the form of a tube. Outer portion 100 includes an entrance region 102 for insertion of any suitable material and/or article, such as the inner portion 10. Outer portion 100 also includes supports 104a and 104b that have an inner width W and a geometry suitable for accommodating placement of the inner portion 10. Collection region 50 is located at the bottom of the outer portion 100 and is suitable for accumulation of the sample (e.g., a solution of fragmented DNA) once the sample has flowed through other regions of the processing device. In some embodiments, an outer portion 100 is a micro centrifuge tube. For example, standard 1.5 or 2 mL micro centrifuge tubes may be used as outer portions of a processing device.

FIG. 2 depicts the structural embodiments of FIGS. 1A and 1B where the inner portion 10 is inserted within the outer portion 100. For example, inner portion 10 is placed into the outer portion 100 through the entrance 102 until an edge of the inlet portion 20 of the inner portion 10 rests against supports 104a and 104b of the outer portion 100. It can be appreciated that supports 104a and 104b are only by way of example and that the inlet portion 20 and shearing region of the inner portion 10 may be associated with an outer portion 100 of a processing device by any suitable manner. For example, inner portion 10 may have an appropriately sized lip that engages with a suitably structured entrance region 102 of the outer portion 100. Or, inner and outer portions 10 and 100 may be coupled together by an adhesive, snap fit, fastener, thermal/ultrasonic sealing or other suitable attachment method. In some embodiments, inner and outer portions of a processing device are manufactured together and do not require a separate insertion step. For example, a processing device having an inlet portion, channel, shearing region and collection portion that can be appropriately coupled to a flow actuator (e.g., centrifuge) may be provided as a single monolithic device. Accordingly, inner and outer portions of a processing device may be integrally formed.

Portions of the processing device may be attached to one another through any appropriate manner. For example, an inlet portion 20 may be attached to a channel 30 and the channel 30 may be further attached to a shearing region. Any appropriate attachment method may be used to attach inner portions of a processing device together, such as for example, an adhesive, snap fit, fastener, thermal/ultrasonic sealing or other suitable attachment method. In some cases, the shape of an inlet portion 20 may facilitate coupling of the inlet portion to a channel and a channel to a shearing region. For example, the inlet portion may have a shape at a distal end region 24 that is suitable to engage with a corresponding shape at an entrance region 32 of an adjacent channel, such as for a snap or interference fit arrangement. Or, the distal end region 24 may simply have a cross sectional area that is similar to a cross sectional area of an entrance region 32 of the adjacent channel, for example, to facilitate an adhesive attachment. Similarly, a channel and a shearing region may be coupled by any suitable method. Portions of the device that are coupled together and in fluid communication will be sufficiently sealed (e.g., gasket, o-ring, vacuum press, etc.) to permit a sample to flow through the processing device without leakage of the sample.

In an illustrative embodiment, a sample containing nucleic acid is introduced into the inlet portion 20 through entrance 22. In some cases, as shown in the figures, the inlet portion is funnel-shaped, facilitating easy entry of the sample into the inlet and subsequent direction of flow of the sample into the shearing region. Accordingly, although the device is not limited as such, a funnel-shaped inlet portion may have an entrance region 22 that has a cross sectional area larger than a cross sectional area of a distal end region 24 of the inlet portion where the distal end region leads toward the shearing region.

Figure 4B:
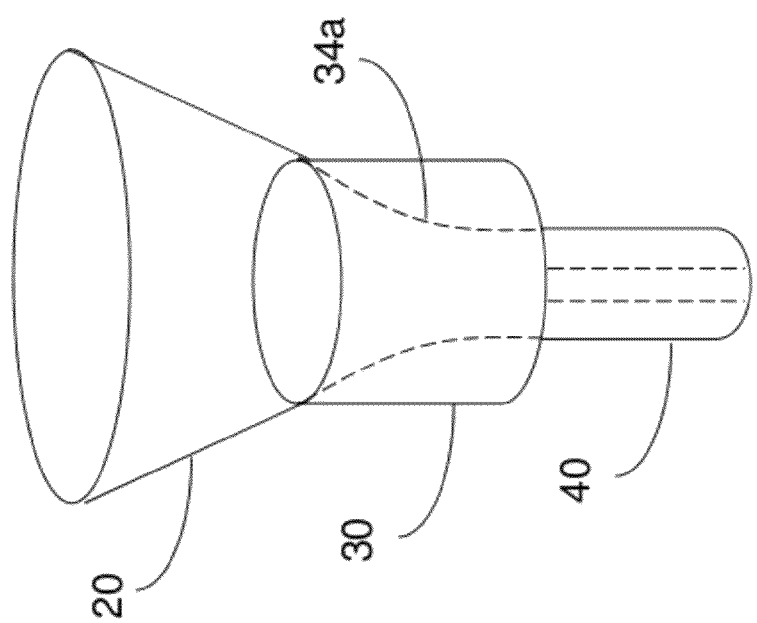
FIG. 4B depicts another embodiment of a processing device for fragmenting nucleic acids.

In embodiments illustrated in FIGS. 4A-4C, the inlet portion 20 is connected to channel 30 in a manner that minimizes the potential for sample to be trapped in various regions of the inlet portion 20. That is, the entire sample flows freely from the inlet portion through the channel 30 and into the shearing orifice 40. In FIG. 4A, channel 30 has an opening 34a that suitably engages with a distal region of inlet portion 20 so as not to give rise to a "dead spot" area where sample material gets stuck and is unable to flow easily between the inlet portion and the channel. Further, a distal portion of the channel 30 has a cross-sectional area that is larger than a cross-sectional area defined by the shearing orifice 40. In FIG. 4B, the opening 34b of the channel 30 has a distal portion that has a cross-sectional area similar in size and shape to that of the diameter of the shearing orifice 40. Accordingly, sample material is able to flow between the opening 34b and shearing orifice 40 without getting trapped at any particular location. Suitable embodiments are not required to have a smooth structural transition between an inlet portion and a channel, or a channel and a shearing orifice. In fact, in some instances, an abrupt transition between various regions such as between the channel and the shearing orifice may be advantageous in providing a structure that gives rise to enhanced shearing, hence, fragmentation of nucleic acids and/or other molecules.

As shown in FIG. 4C, the processing device of FIG. 4A is disposed at an angle (e.g., 45 degrees) commonly associated with placement in a centrifuge. Upon activation of the centrifuge, the processing device rotates about rotational axis A. Accordingly, sample flows through the inlet portion 20 depicted by dashed direction arrows $F_1$ and into channel 30 as shown by dashed direction arrows $F_2$. The opening 34 in channel 30 provides ease of flow from the inlet portion through the channel and into the shearing orifice 40. In some embodiments, the geometry of a distal end region of the channel 30 and the entrance to a shearing orifice 40 includes an inner wall having an angle that is substantially perpendicular to the direction of flow of the sample through the shearing orifice, indicated by dashed direction arrows $F_4$. Accordingly, flow of sample from the channel to the shearing orifice changes abruptly, giving rise to an enhanced shearing effect. In some cases, such a wall at the entrance to the shearing orifice may be positioned at the exterior of the orifice. As sample flows through the entrance the shearing orifice 40 and through the rest of the shearing region, a shearing force is applied to the sample containing nucleic acids in a manner that fragments the nucleic acids.

The pressure at the shearing orifice 40 in an arrangement like that shown in FIG. 4C may depend on several parameters, including a density of the sample fluid (p), an angular speed of the centrifuge (ω), a radius (r) of the shearing orifice from the axis of rotation (A), and a height of the fluid (h) above the shearing orifice. In one embodiment, the following equation gives the pressure (P):

$$P = \frac{\rho \omega^2 (r^2 - (r-h)^2)}{2}$$

The flow rate through the orifice 40 may depend on several parameters, including the pressure at the entrance to the orifice (P1), a pressure at the exit of the orifice (P2), the internal diameter of the orifice (D1), an external diameter of the orifice (D2), and the density (ρ). In one embodiment, the following equation gives the flow rate Q:

$$Q = \sqrt{\frac{1}{1 - \left(\frac{D_2}{D_1}\right)^4}} \frac{\pi D_2^2}{4} \sqrt{\frac{2(p_1 - p_2)}{\rho}}$$

Thus, the flow rate (and shearing of molecules at the orifice) in a centrifuge application depends on the angular speed of the centrifuge, the diameter of the orifice, the radius of the orifice from the axis of rotation, and the height of the sample over the orifice. The angular speed, diameter of the orifice and radius of the orifice can all be closely controlled, and made constant if desired. Only the sample height over the orifice will vary, and thus to maintain closer control over shearing, the inlet (e.g., inlet portion and channel) is ideally arranged to maintain the sample head height over the orifice to be as constant as possible during processing. In an arrangement like that illustrated in FIG. 1A, if the volume of the channel 30 is relatively small, and the inlet portion 20 is arranged to minimize the change in sample height as sample is drawn from the inlet portion 20, the height (and thus sample pressure) at the orifice may be relatively constant. Also, a relatively small volume for the channel 30 will result in only a relatively small amount of the sample being forced through the orifice at a lower pressure than other portions of the sample.

Fragmenting of nucleic acids within samples to average nucleic acid sizes that are less than or equal to half the original nucleic acid size before processing may occur within a generally short period of time. In some embodiments, a force (e.g., from a flow actuator such as a centrifuge or pump) is applied to a sample containing nucleic acids to induce flow of the sample only once through a shearing region of a processing device where the final average nucleic acid size of the sample is less than or equal to about half the initial average nucleic acid size in the sample from before application of the force. However, it should be appreciated that flow through certain processing devices contemplated herein may occur multiple times, for example, in providing for a refined distribution of nucleic acid sizes. In some embodiments, the force that causes a sample with nucleic acids to flow through a shearing region of a processing device is applied for a minute or less (e.g., for 30 seconds or less), and the final average nucleic acid size of the sample is less than or equal to about half the initial average nucleic acid size in the sample prior to application of the force.

Any suitable sample containing nucleic acids having an initial average nucleic acid size may be supplied to the processing device. For example, a sample may include a liquid solution having an appropriate concentration of nucleic acids contained within the solution. Prior to fragmentation in the processing device, samples of nucleic acids may have any suitable initial average nucleic acid size, for example, between about 40 kbp and about 50 kbp (e.g., about 48 kbp), between about 40 kbp and 100 Mbp, between about 40 kbp and 1 Gbp (e.g., on the order of genomic sized nucleic acids), between about 1 Mbp and 100 Mbp, between about 40 kbp and 1 Mbp. Nucleic acids may include macromolecules such as DNA, RNA, or other suitable nucleotide-based compounds. A sample containing nucleic acids to be introduced into a processing device can also be of any suitable volume. In some embodiments, a sample volume may range between about 50 microliters and about 500 microliters.

A force applied to a sample disposed within a processing device and containing nucleic acids may induce the sample to flow through the processing device from the inlet (e.g., including a channel) through a shearing region and into a collection region. In some cases, such a force can be applied to the sample in a manner that pushes the sample from the inlet through a shearing region of a processing device by using a pump, such as a syringe arrangement. However, in some embodiments, a force applied to the sample to induce flow of the sample from the inlet through the shearing region occurs without contact of the sample with a pump or syringe arrangement. For example, a processing device may be placed within an appropriate region of a centrifuge where a force generated by the centrifuge is applied to the device so that the sample flows through the shearing region and into the collection portion. In some embodiments, the sample is forced to flow from the inlet through the shearing region by the application of an air induced pressure. For example, a gas pressure supply may be suitably coupled to the processing device so as to generate a force that causes the sample to flow through the shearing region. Alternatively, a negative vacuum pressure could also be used to force the sample through the shearing region. Moreover, in some embodiments, appropriate movement or agitation of the processing device induces sample flow from the inlet through the shearing region. For example, the processing device may be subject to a shaking motion or other appropriate acceleration to cause sample to flow through the shearing region.

In some embodiments, the entire sample volume that is introduced into the inlet of the processing device flows through the shearing region and may be recovered at the collection portion. In conventional situations where, for example, a syringe holding a sample is used to pump the sample from an inlet through a shearing region, a small portion of the sample remains as a small unused volume at the region of the syringe that contacts the sample. Thus, using a syringe to pump the sample from the inlet through the shearing region gives rise to a fractional loss of sample that cannot ultimately be recovered after processing. On the other hand, producing a force that does not involve contact of the sample with a pump, such as for example, with a centrifuge or a pump that supplies suitable force without direct contact, permits the entire volume of the sample to travel from the inlet through the shearing region and ultimately into a collection portion for full recovery of processed sample.

Fragmented nucleic acids within processed samples may have a desired range of final average nucleic acid sizes. In some embodiments, a final average nucleic acid size of a processed sample ranges between about 5 kbp and about 20 kbp; between about 5 kbp and about 10 kbp; less than about 10 kbp; between about 8 kbp and about 20 kbp; or between about 10 kbp and about 20 kbp. In some cases, the degree to which nucleic acid sizes are fragmented may depend on various factors, such as the force (e.g., generated by varying speed of a centrifuge or a distance of the shearing region to a center of rotation of the centrifuge) applied to the sample that causes the sample to flow through the shearing region. For example, applying an increasing force to a sample may increase the shear forces applied to nucleic acids within the sample, yielding smaller nucleic acid fragments. The concentration of nucleic acids in a solution may also contribute to the final average nucleic acid size. Accordingly, for certain cases, a greater concentration of nucleic acids in a solution may result in slower fragmentation of the nucleic acids, resulting in a larger average value of nucleic acid fragments. Nucleic acid concentrations in a sample may vary, for example, between about 5 micrograms/milliliter and about 200 micrograms/milliliter, but are not so limited in range or distribution. In some embodiments, the fragment size distribution of processed nucleic acid is less than about 14 fold; less than about 7 fold; or less than about 2 fold. In an example, for an average nucleic acid size of about 10.5 kbp, the variation of fragmented nucleic acid is between about 7 fold and about 14 fold.

Flow of a sample through a processing device may occur at any appropriate rate. Accordingly, the greater the force applied to the sample, the greater the rate of sample flow through the processing device will likely be, depending, of course, on other factors such as the orifice size at the shearing region. In some embodiments, the flow rate of a sample through a processing device at any given time during processing can be, for example, less than about 3 microliters/second; between about 1 microliter/second and about 3 microliters/second; or between about 1.5 microliters/second and about 2.5 microliters/second. In some embodiments, the flow rate of a sample through a processing device at any given time during processing can be, for example, less than about 20 microliters/second; or between about 10 microliters/second and about 20 microliters/second. Other flow rates of sample through a processing device are possible.

The flow rate of a sample through a processing device, at various points during processing, may change according to any suitable degree. In some embodiments, the flow rate of the sample through the processing device remains relatively constant during a majority of sample flow through the shearing region. For example, the flow rate of a sample through the processing device may be considered to be a constant flow rate when, during a majority of the processing time for the sample, the flow rate does not change by more than about 50%; more than about 40%; more than about 30%; more than about 20%; more than about 15%; or more than about 10% of the initial flow rate through the processing device.

A processing device may be manufactured to be disposable. That is, upon a single usage, once the sample is processed and collected, the device may be suitably eliminated. Accordingly, as disposable processing devices are not reused (or washed and reused), the possibility of cross contamination between samples is significantly reduced.

Shearing orifices may include any suitable material. In some embodiments, a shearing orifice includes ruby, sapphire, glass, polyether ether ketone (PEEK), polyimide, stainless steel, other suitable materials or combinations thereof. In some embodiments, a shearing orifice includes a coating material, such as polyimide. For example, application of a coating material may decrease the potential for clogging as particular coatings may lessen the likelihood for nucleic acids to bind to surfaces of a shearing orifice.

Figure 5:
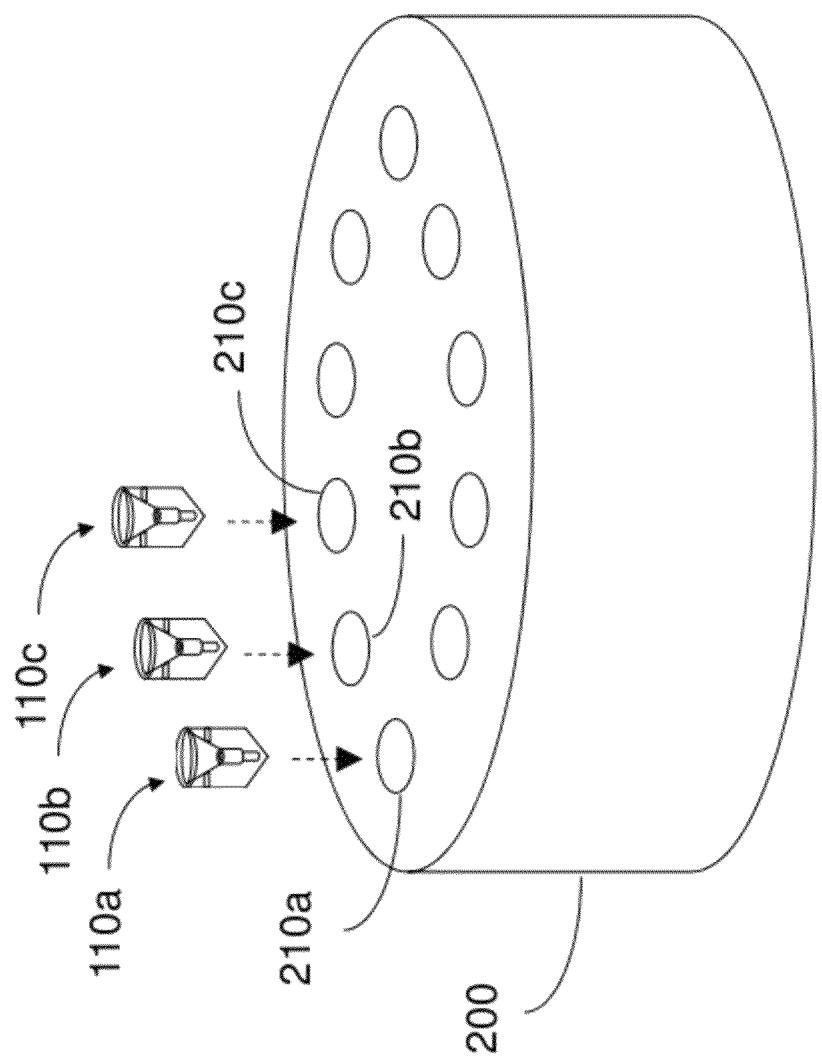
FIG. 5 depicts processing devices and a centrifuge in accordance with an illustrative embodiment.

FIG. 5 depicts an illustrative embodiment of a centrifuge 200 having receiving regions 210a, 210b and 210c into which separate processing devices 110a, 110b and 110c are appropriately inserted. Disposed within each of processing devices 110a, 110b and 110c are respective samples containing nucleic acids. Processing devices are inserted into appropriate receiving regions of the centrifuge 200 as depicted by the dashed arrows. The centrifuge is then activated to generate a force that causes samples within each of the processing devices to flow from respective inlet portions through shearing regions and into collection portions of the devices.

A centrifuge may have any suitable number of receiving regions within which processing devices may be placed. Activation of the centrifuge produces a force that induces simultaneous flow of samples having nucleic acids through shearing regions of each of the respective processing devices. In some embodiments, as shown in FIG. 5, a centrifuge includes ten receiving regions. In other embodiments, a centrifuge includes twelve or more receiving regions. Accordingly, a centrifuge is able to impart a force that brings about simultaneous nucleic acid fragmentation to as many processing devices as the centrifuge has receiving regions. In some cases, a high speed centrifuge may be used to generate forces that lead to nucleic acid shear in processing devices described. For example, a suitable centrifuge may generate forces at rotational velocities greater than or equal to 8000 rpm, greater than or equal to 10000 rpm, greater than or equal to 12000 rpm, or greater than or equal to 14000 rpm.

Systems and methods that incorporate processing devices described for fragmenting nucleic acids may afford several benefits, such as for example, yielding a desirable range and distribution of sizes for nucleic acid fragments, eliminating cross contamination, having the ability to process a variety of different sample volumes and concentrations, processing of samples simultaneously, no sample loss, and short processing times. Various embodiments of processing devices that provide the above benefits, in addition to those already discussed, will now be described.

Figure 6:
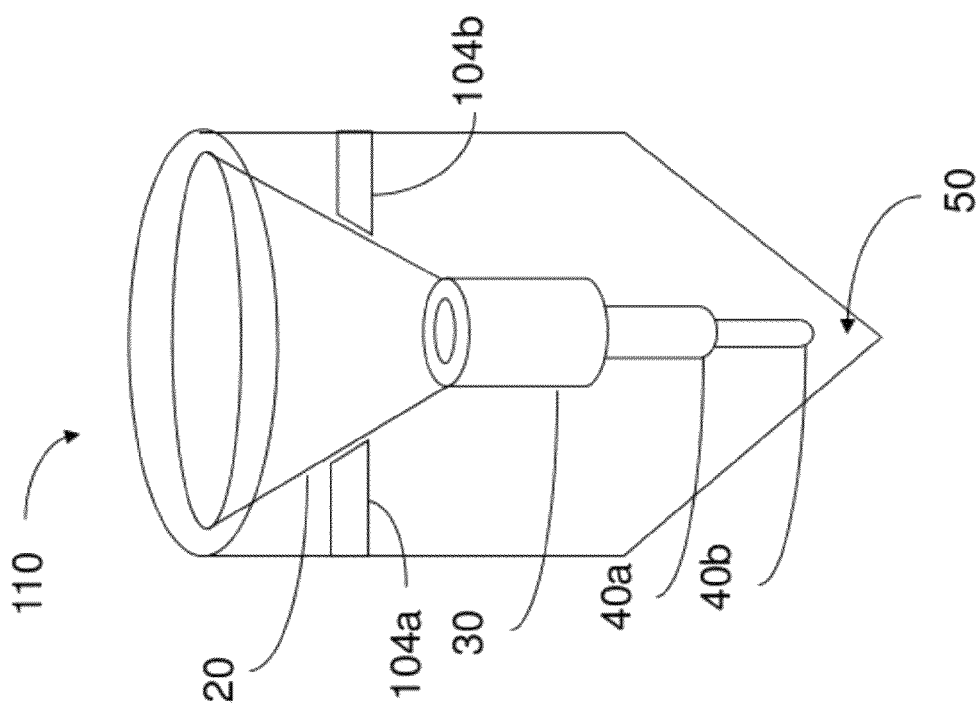
FIG. 6 illustrates an embodiment of a processing device suitable for fragmenting nucleic acids.

A shearing region may include any suitable number of shearing orifices through which a sample may flow. In an illustrative embodiment shown in FIG. 6, the shearing region of a processing device 110 includes two shearing orifices 40a and 40b disposed in a series arrangement. Although not expressly shown in the figures, it can be appreciated that more channels and/or shearing orifices may also be included in a processing device. For example, one or more channels may be included in between or downstream from shearing orifices 40a and 40b.

Figure 7:
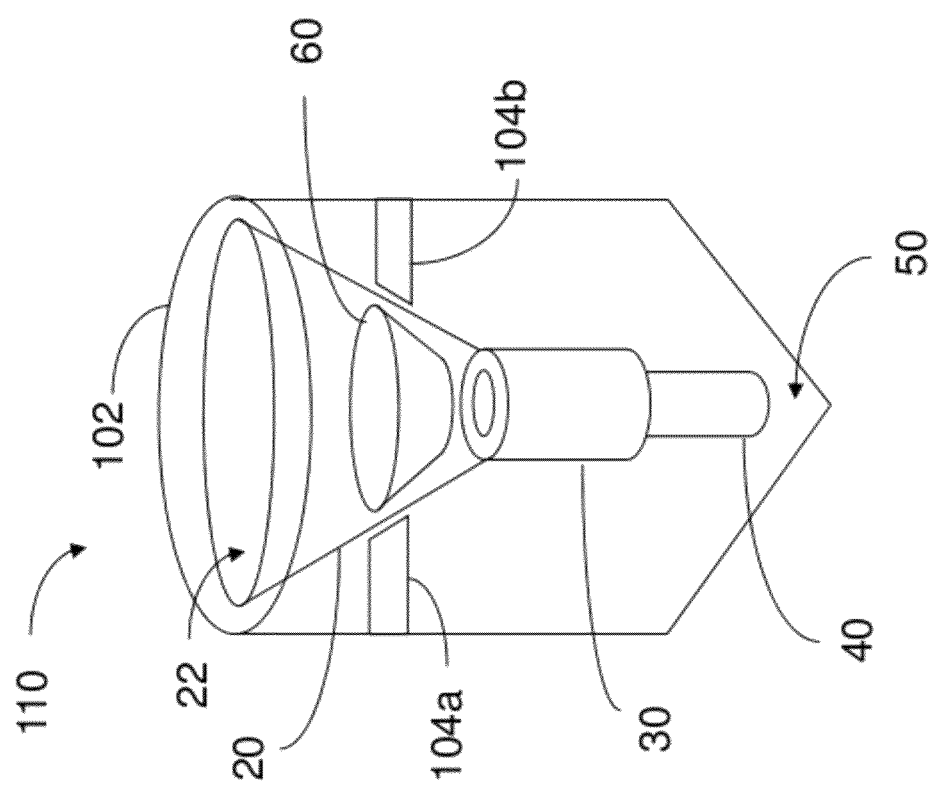
FIG. 7 shows another illustrative embodiment of a processing device suitable for fragmenting nucleic acids.

In some embodiments, a processing device includes a filter. FIG. 7 depicts an illustrative embodiment where a filter 60 is disposed within an inlet portion 20 of the processing device 110. Accordingly, the filter 60 serves to prevent contamination or clogging of material as sample flows from the inlet portion 20 and into the shearing region. While certain materials are not permitted to flow through the filter, a suitable fluid sample may pass through the filter and into the shearing region. In embodiments where a centrifuge is used to generate force that induces a sample to flow from the inlet through the shearing region, a filter may serve to slow down initial flow of sample near an entrance of the shearing region. Accordingly, in some cases, a majority of the sample disposed within the inlet has not yet entered into the shearing region until the centrifuge has reached a steady state angular velocity. In some cases, a filter 60 is disposed above channel 30 or is positioned high enough within the inlet portion 20 not to interfere with pressure established by the sample at the entrance of shearing orifice 40 during processing for efficient shearing of nucleic acids. In some embodiments, the distance between a filter 60 and a shearing orifice 40 is between about 5 mm and about 20 mm.

It can be appreciated that a filter can be appropriately positioned within an inlet by any suitable method. In some non-limiting examples, a filter may simply be placed at a distal end region of the inlet portion adjacent to the entrance of the shearing region without attachment, or a filter may be attached by an adhesive or attachment point to a portion of the inlet or shearing region.

In some embodiments, to prevent material from exiting or from entering the entrance region of the inlet portion, a processing device includes a cap. FIG. 8 shows an illustrative embodiment where a cap 106 is disposed over an inlet portion 20 of the processing device 110. The cap 106 may be coupled to the inlet portion 20 by any suitable method, for example, by an adhesive, a snap fit, screw fit or another appropriate attachment. When the cap 106 is appropriately coupled to the entrance of inlet portion 20, the cap 106 blocks outside material from entering into the inlet portion and contaminating contents within the processing device. The cap 106 also serves to block material within the inlet portion from being removed, such as through splashing caused by sudden movement of the device.

As discussed above, a shearing region can have one or more channels and/or shearing orifices. FIGS. 9-11 depict an illustrative embodiment of a channel 30 and a shearing orifice 40 disposed adjacent one another in a series arrangement. In this embodiment, when a suitable force is applied to the device, a sample flows into an entrance and through an opening of the channel 30 and subsequently flows through a shearing orifice 40 for fragmentation. Although not required, both the channel and the shearing orifice are cylindrical in shape.

FIG. 9 shows a side view of a channel 30 and a shearing orifice 40. Channel 30 has a first length $L_1$ and shearing orifice 40 has a second length $L_2$. Channels and shearing orifices presented herein may have any suitable length. In some embodiments, a length of a channel ranges between about 5 mm and about 20 mm; between about 10 mm and about 15 mm; between about 100 microns and about 20 mm; or between about 100 microns and about 5 mm. In some embodiments, a length of a shearing orifice is between about 100 microns and about 20 mm; between about 100 microns and about 5 mm; between about 5 mm and about 20 mm; between about 200 microns and about 500 microns; or greater than about 250 microns.

FIG. 10 illustrates a cross sectional view of channel 30, through a corresponding line depicted in FIG. 9, where the channel 30 has an inner surface 36 of an orifice into which sample may flow from the inlet of the processing device. Channel 30 also includes an outer surface 38. As illustrated in FIG. 10, inner surface 36 has an inner width $W_1$ and outer surface 38 has an outer width $W_2$.

FIG. 11 shows a cross sectional view of shearing orifice 40 through a corresponding line depicted in FIG. 9. Shearing orifice 40 includes an inner surface 46 of an orifice into which sample may flow from the channel 30. Shearing orifice 40 also includes an outer surface 48. Shown in FIG. 11, inner surface 46 has an inner width $W_3$ and outer surface 48 has an outer width $W_4$.

It can be appreciated that inner and outer widths of channels and shearing orifices may be any suitable size. However, in the embodiment illustrated in FIGS. 9-11, although not required for every embodiment, the inner width $W_1$ of a channel 30 is equal to the outer width $W_4$ of shearing orifice 40. In some embodiments, an inner width of a shearing orifice through which sample may flow ranges between about 10 microns and about 100 microns; between about 10 microns and about 50 microns; or between about 10 microns and about 70 microns. In some embodiments, an inner width of a channel ranges between about 300 microns and about 2 mm. In some embodiments, an outer width of a shearing orifice is greater than about 50 microns; between about 50 microns and about 1 mm; between about 100 microns and about 1 mm; or greater than about 1 mm. For example, an outer width of a shearing orifice can range between about 300 microns about 1.5 mm.

The width of a shearing orifice can affect the degree to which shearing force is applied to nucleic acids in a sample. For example, a smaller orifice width may give rise to a greater degree of shearing force applied to the nucleic acids upon flow of sample into and through the orifice, hence, leading to an increased degree of nucleic acid fragmentation.

In an example, a shearing orifice has an inner diameter of about 30 microns, an outer diameter of about 1.5 mm and a length of about 250 microns. The channel has an inner diameter of about 1.5 mm and a length of about 10 mm.

A number of shearing orifices may be included in a shearing region through which samples containing nucleic acid may flow. FIG. 12 depicts an illustrative embodiment of a shearing region 41 having four orifices defined by surfaces 46a, 46b, 46c and 46d. Accordingly, upon application of an appropriate force, sample flows from an inlet into and through each of the orifices in parallel in the shearing region. In one embodiment, a number of holes approximately 40 microns in diameter are drilled into a polyimide film about 250 microns thick where the holes are spaced apart by a center to center spacing greater than about 200 microns (e.g., a center to center spacing of about 250 microns).

It can also be appreciated that orifices of a shearing region may have any suitable shape. FIG. 13 illustrates a non-limiting embodiment of a shearing region 41 having four orifices defined by surfaces 46e, 46f, 46g and 46d that are of varying shapes. For example, surface 46e defines a rectangular/square shape; surface 46f defines a triangular shape; surface 46g defines an elliptical shape; and surface 46h defines a hexagonal shape. When a suitable force is applied, sample containing nucleic acid flows through each of the orifices disposed in the shearing region 41.

It should be appreciated that channels may also have any suitable number of openings through which samples containing nucleic acid may flow. Such channel openings may also have any suitable shape.

Figure 14:
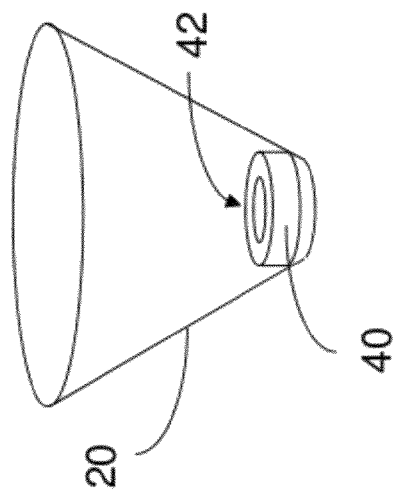
FIG. 14 shows portions of a processing device suitable for fragmenting nucleic acids in accordance with an illustrative embodiment.

A shearing orifice may be coupled with an inlet of a processing device in any suitable manner. For example, FIG. 14 illustrates an embodiment of a shearing orifice 40 disposed between walls of an inlet portion 20 of a processing device (the outer portion and collection region are not shown). In use, sample is added into the inlet portion 20 and the processing device is placed in a centrifuge. Upon activation of the centrifuge, the sample moves through the entrance 42 of the shearing orifice 40. The sample then travels out of the shearing orifice 40 into a distal end portion of the inlet portion 20 and into another shearing orifice or a collection region (not shown in FIG. 14). In some embodiments, the shearing orifice 40 and the inlet portion 20 are arranged such that upon processing of a sample, some of the sample remains within the inlet portion.

Figure 15:
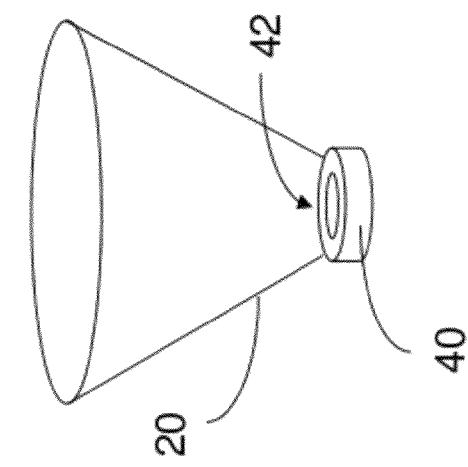
FIG. 15 depicts portions of a processing device suitable for fragmenting nucleic acids in accordance with another illustrative embodiment.

FIG. 15 depicts an embodiment of a shearing orifice 40 disposed beneath walls of an inlet portion 20 where an outer portion and collection region for placement in a centrifuge are not shown. As described for FIG. 14, the sample is introduced into the processing device through inlet portion 20, the processing device is placed in a centrifuge, and the centrifuge is activated. Upon application of force from the centrifuge, the sample moves through the body of the inlet to a distal end portion of the inlet where the sample then flows through entrance 42 of the shearing orifice 40. Upon exiting from shearing orifice 40, the sample subsequently flows into another shearing orifice or a collection region (not shown in FIG. 15). While no channel is expressly shown, one or more channels may be incorporated in the embodiment in a suitable manner.

Figure 16:
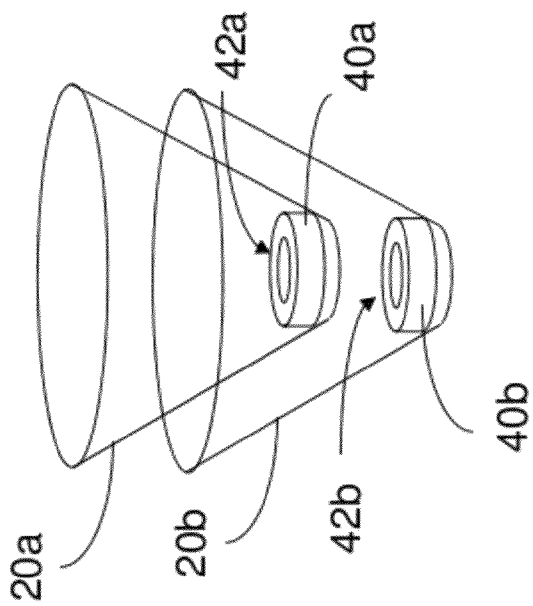
FIG. 16 depicts portions of a processing device suitable for fragmenting nucleic acids in accordance with a different illustrative embodiment.

FIG. 16 shows an embodiment of a processing device where a portion of a first inlet portion 20a having a corresponding shearing orifice 40a of a processing device is disposed within a second inlet portion 20b having a corresponding shearing orifice 40b. In use, after sample is introduced to an entrance of the first inlet portion 20a, a processing force (e.g., from a centrifuge) is applied to the device. The sample flows through the entrance 42a of the shearing orifice 40a, and then out of the shearing orifice 40a. The sample subsequently reaches the second inlet portion 20b where the sample eventually flows through shearing orifice 40b via the corresponding entrance 42b and possibly a suitable channel. From shearing orifice 40b, the sample flows into a subsequent shearing orifice or a collection region (not shown in FIG. 16). In some cases, upon application of a processing force, having multiple inlet portions in a processing device may result in samples experiencing an increase in nucleic acid fragmentation as the sample flows through the device, giving rise to processed samples having nucleic acids with generally smaller average fragment sizes and/or an increased uniformity of fragment sizes in the finished sample. One or more channels may be suitably incorporated with the shearing orifices.

Figure 17:
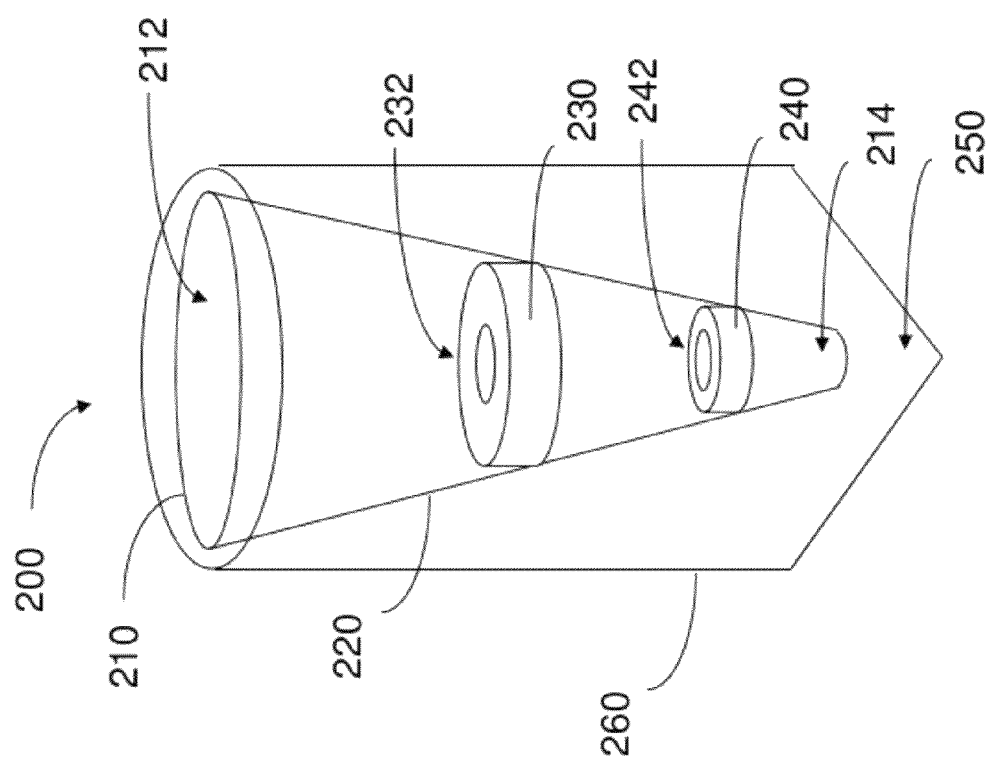
FIG. 17 illustrates an embodiment of a processing device for fragmenting nucleic acids.

FIG. 17 shows an illustrative embodiment of a processing device 200 that may be used for fragmenting nucleic acids. The processing device 200 includes an inner portion 210 through which a solution of nucleic acids may flow and an outer portion 260 that is built for placement within a receiving area of a centrifuge. The inner portion 210 includes an inlet reservoir 220, a shearing region comprising a first shearing orifice 230 and a second shearing orifice 240, and collection region 250. A sample containing nucleic acids (e.g., a liquid solution with DNA) is introduced into an entrance 212 of the inlet reservoir 220 and the device 200 is suitably placed in a centrifuge for processing.

Once the centrifuge is activated to generate a force to induce the sample to move through the processing device, the sample flows through the entrance 232 of the first shearing orifice 230 and is fragmented by the shear forces associated with the shearing orifice 230. The sample subsequently flows out of the shearing orifice 230 and continues to travel through the inlet reservoir 220 reaching the second shearing orifice 240. The sample then flows into the entrance 242 of the second shearing orifice 240 and nucleic acids within the sample are fragmented by shear forces that arise from the second shearing orifice 240. The sample then flows out toward distal end region 214 of the inlet reservoir 220. As the centrifuge continues to spin, the sample containing fragmented nucleic acids accumulates at the collection region 250. Or, alternatively, the distal end region 214 may be closed off such that the sample collects at the bottom of the inlet reservoir 220 without passing through into the collection region 250. Accordingly, the distal end region 214 may serve as the collection region. Shearing orifices 230 and/or 240 may be disposed at any suitable location along the inlet reservoir 220, but in some embodiments, providing a suitably long distance between orifices 230 and 240 may help establish a desired sample pressure at the downstream orifice 240. That is, an effective decoupling of fluid between the orifices 230 and 240 may be established so that pressure at the upstream orifice 230 does not influence pressure at the downstream orifice 240. In some embodiments, shearing orifices are disposed between about 5 mm and about 20 mm from one another. Although not explicitly shown, it should also be appreciated that inlet reservoir 220 and outer portion 260 may be attached or coupled together by any suitable method. In some embodiments, inlet reservoir 220 and outer portion 260 may integrally formed together as a single monolithic device.

Inlet reservoir 220 of the processing device is illustrated in FIG. 17 to have a conical shape, though it should be understood that inlet reservoirs may have any appropriate shape. For example, a suitable inlet reservoir in accordance with embodiments described may be straight or may include an appropriate curvature.

In some embodiments, channels are disposed between shearing orifices. For example, a processing device not expressly shown in the figures may include an inlet reservoir 220, a first channel, a first shearing orifice 230, a second channel and a second shearing orifice 240, disposed in a series arrangement where channels and shearing orifices are in fluid communication. In such an example, once the centrifuge is activated, the sample flows through the first channel and into the entrance 232 of the first shearing orifice 230 for fragmentation by the shear forces corresponding to the shearing orifice 230. The sample subsequently flows out of the shearing orifice 230 and through the second channel to reach the second shearing orifice 240. The sample then flows into the entrance 242 of the second shearing orifice 240 and nucleic acids within the sample are appropriately fragmented. Channels between shearing orifices may have any suitable dimensions, such as those ranges for length, inner width and outer width as described previously. In some embodiments, a processing device having two or more shearing orifices may include an inlet portion and one or more channels that are structured such that a sample height above each shearing orifice, hence the pressure at the entrance of a corresponding shearing region and the flow rate through the device as well, remains relatively constant during flow of a majority of the sample through processing device.

Figure 18:
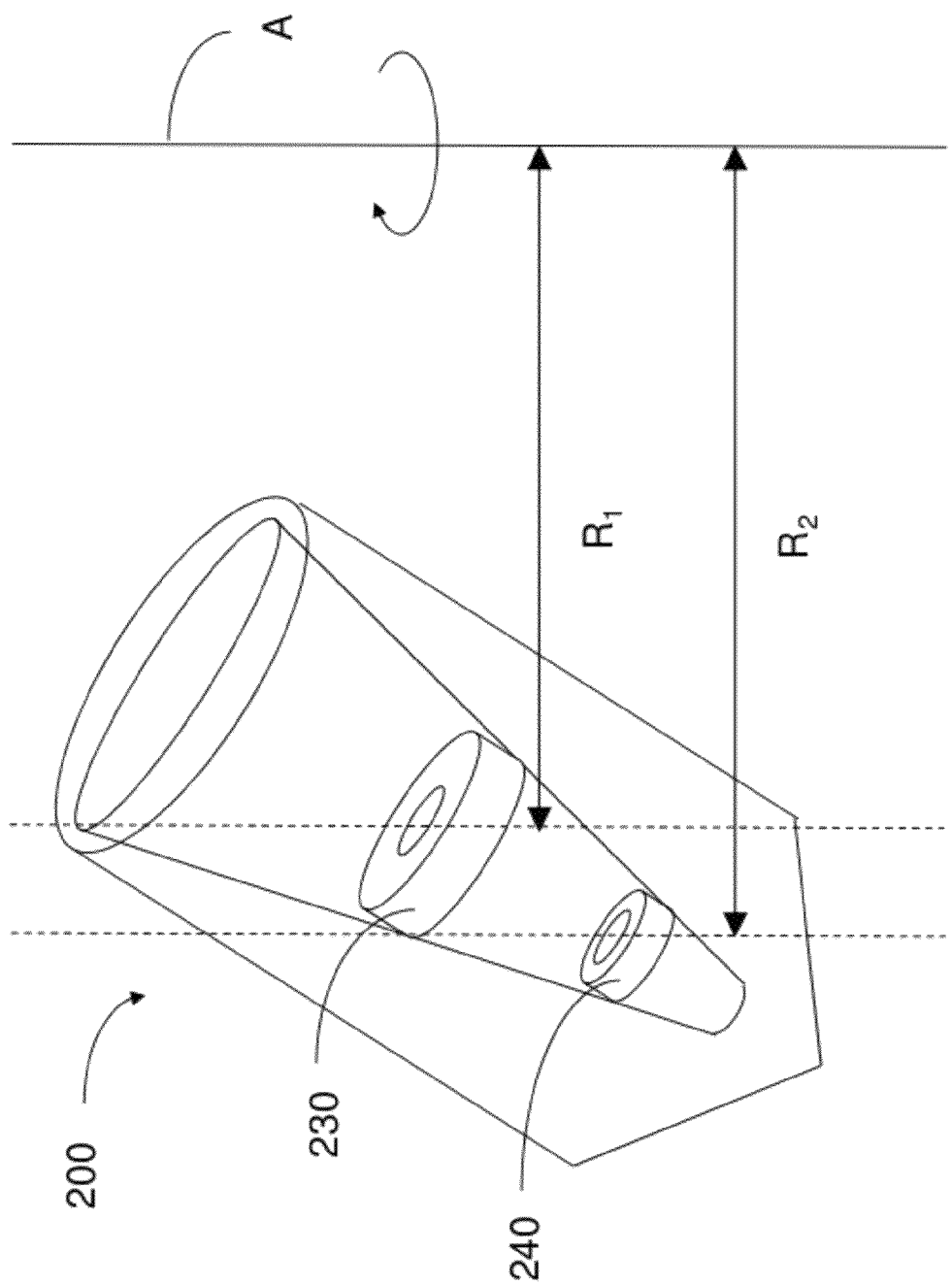
FIG. 18 depicts the processing device of FIG. 17 disposed about a rotational axis according to an illustrative embodiment.

FIG. 18 illustrates a processing device 200 having an orientation when suitably placed in a centrifuge where the device is in a tilted arrangement such that the center of first shearing orifice 230 is disposed a radial distance $R_1$ away from the rotational axis A of the centrifuge. Similarly, the center of second shearing orifice 240 is disposed a radial distance $R_2$ away from the rotational axis A of the centrifuge. Due to the tilted configuration of the processing device, radial distance $R_1$ is less than radial distance $R_2$.

In some cases, various features of the processing device and centrifuge system may influence sample flow rate through shearing orifices, and thus, the ability for nucleic acids in a sample to be fragmented. Such features may include, for example, the rotational speed of the centrifuge, the diameter of shearing orifices, and the radial distances of the shearing orifices from the rotational axis. In some embodiments, the location of shearing orifices along an inlet reservoir may have some influence on the degree of fragmentation of nucleic acids. For example, a first shearing orifice positioned closer to an entrance of an inlet reservoir (and thus at a smaller radius from the centrifuge's axis of rotation A, e.g., radial distance $R_1$) and having a given diameter may exhibit a slower flow rate through the orifice than a second shearing orifice with the same diameter and positioned closer to a distal end of the inlet reservoir (and thus at a larger radius R from the centrifuge's axis of rotation A than the first shearing orifice, e.g., radial distance $R_2$).

In some cases, a slower sample flow rate through a shearing orifice gives rise to a decrease in shear force, and hence, a decrease in nucleic acid fragmentation. In fact, for any given centrifuge system, the final average nucleic acid size and distribution after processing can depend on particular geometrical design considerations of the processing device. Accordingly, specific target ranges of nucleic acid sizes can be recovered based on certain attributes of processing devices used in certain processing systems. In some embodiments, processing devices are tunably designed to yield particular ranges of nucleic acid size upon processing. For example, the orifice size, radius R from the axis of rotation A, and/or sample head height over each respective orifice may be designed to provide identical or nearly the same shearing affect at both orifices 230 and 240 in a device like that in FIG. 18. Though not shown, each orifice 230 and 240 may have respective inlet portions/channels that help to define a head height of the sample for the associated orifice. In some embodiments, shearing orifices 230 and 240 may share the same collection region where sample material flows through both orifices and into the collection region. In other embodiments not shown in the figures, separate and independent shearing orifices may have respective collection regions where sample material flows separately through each orifice and is independently collected.

Referring again to FIGS. 17 and 18, in some embodiments, the flow rate of a sample through the second shearing orifice 240 is kept generally constant so as to result in a relatively small nucleic acid size variation on recovery of the sample. To accomplish this, during most of the processing time, the volume of sample disposed between the first and second shearing orifices 230 and 240 remains generally constant. Accordingly, in an embodiment, sample flows more readily through the first shearing orifice 230 than flow of the sample through the second shearing orifice 240. Further, to accommodate for the radial distance $R_1$ of the first shearing orifice 230 being smaller than the radial distance $R_2$ for the second shearing orifice 240, the diameter of the first shearing orifice 230 may be larger than the diameter of the second shearing orifice 240. Thus, when the centrifuge is activated, although the flow force that moves the sample through the second shearing orifice 240 may be greater than the flow force that moves the sample through the first shearing orifice 230, the larger diameter of the first shearing orifice 230 allows the volume of sample disposed between the first and second shearing orifices 230 and 240 to remain generally constant as the sample material moves through the device.

Figure 19:
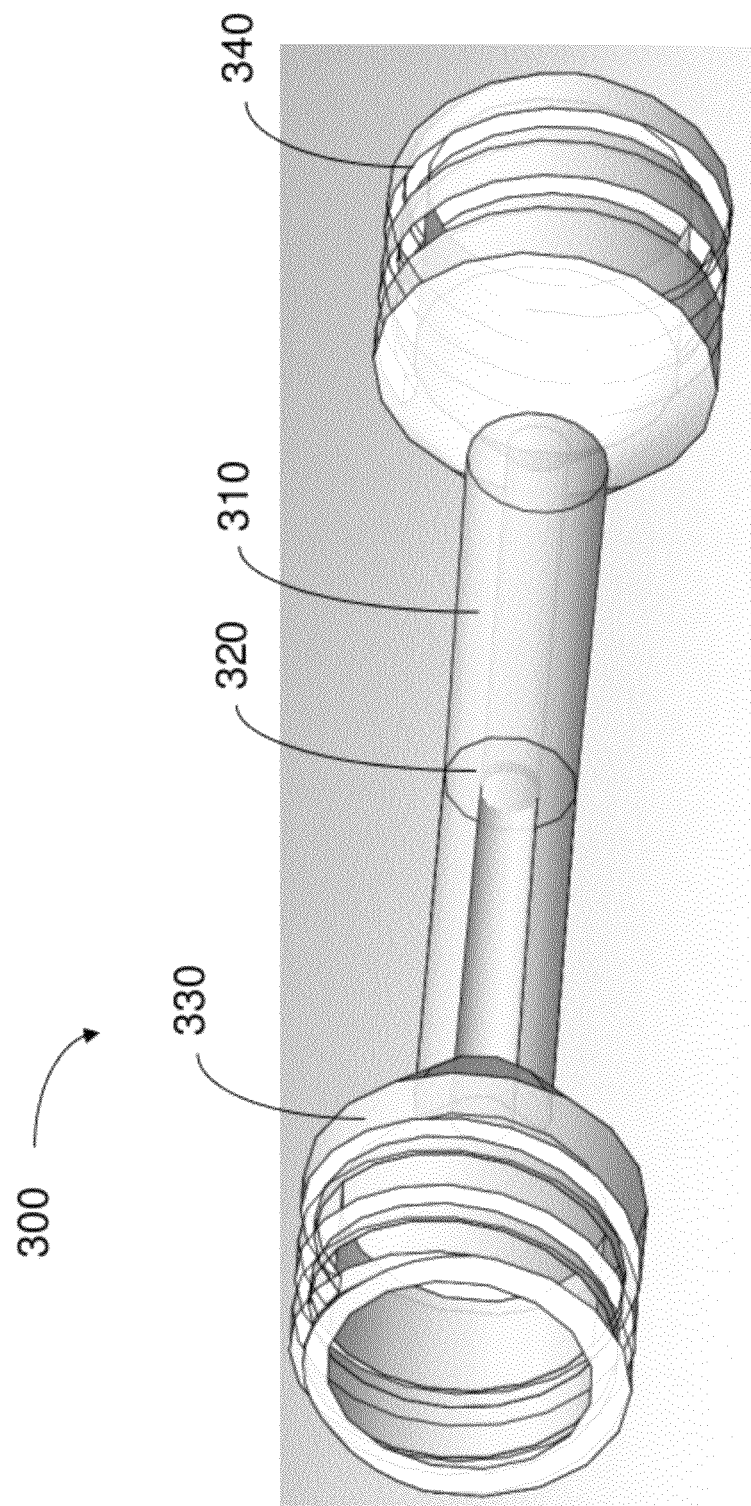
FIG. 19 shows a perspective view of another illustrative embodiment of a processing device.
Figure 20A:
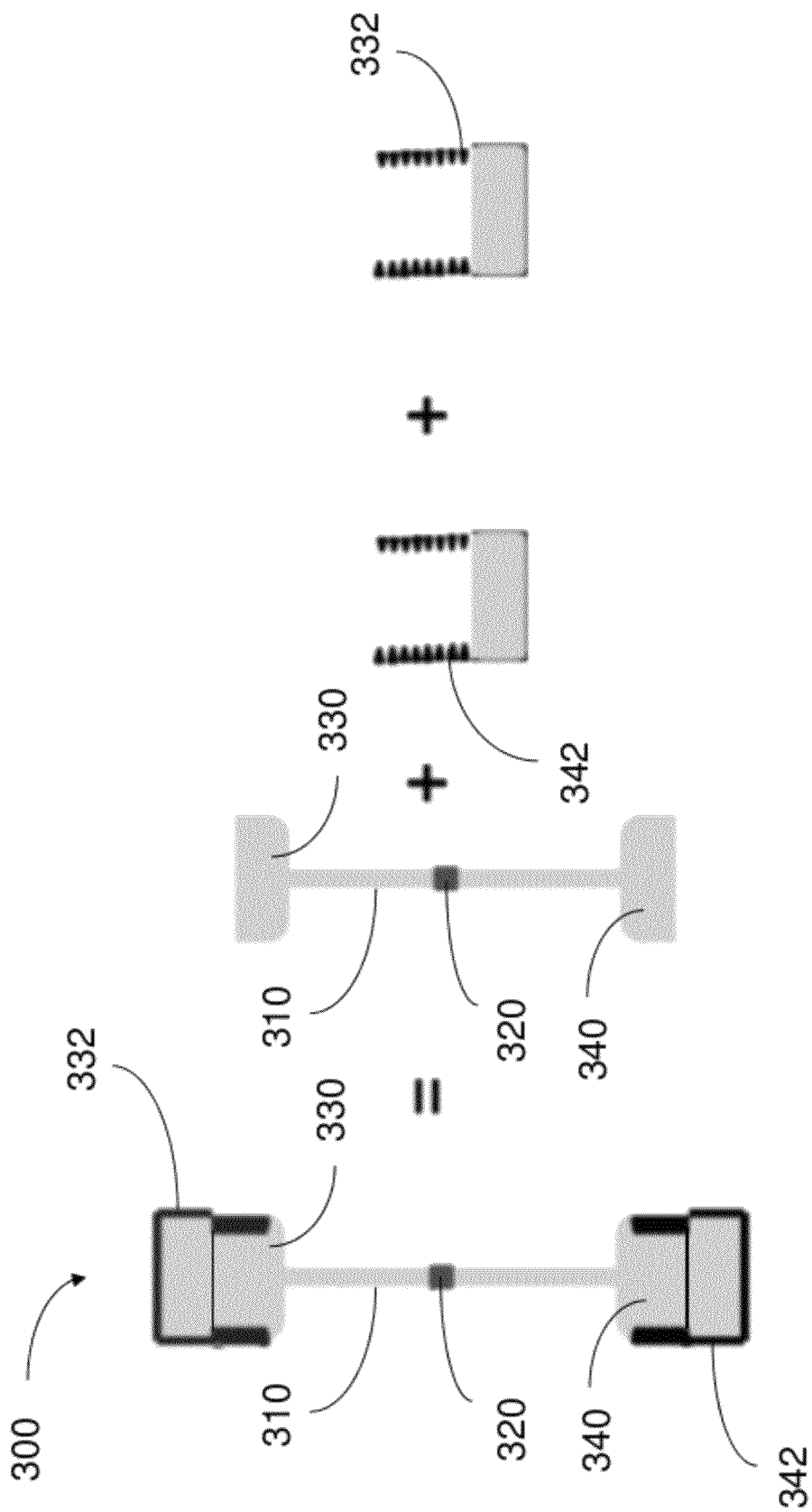
FIG. 20A illustrates yet another embodiment of a processing device for fragmenting nucleic acids.
Figure 20B:
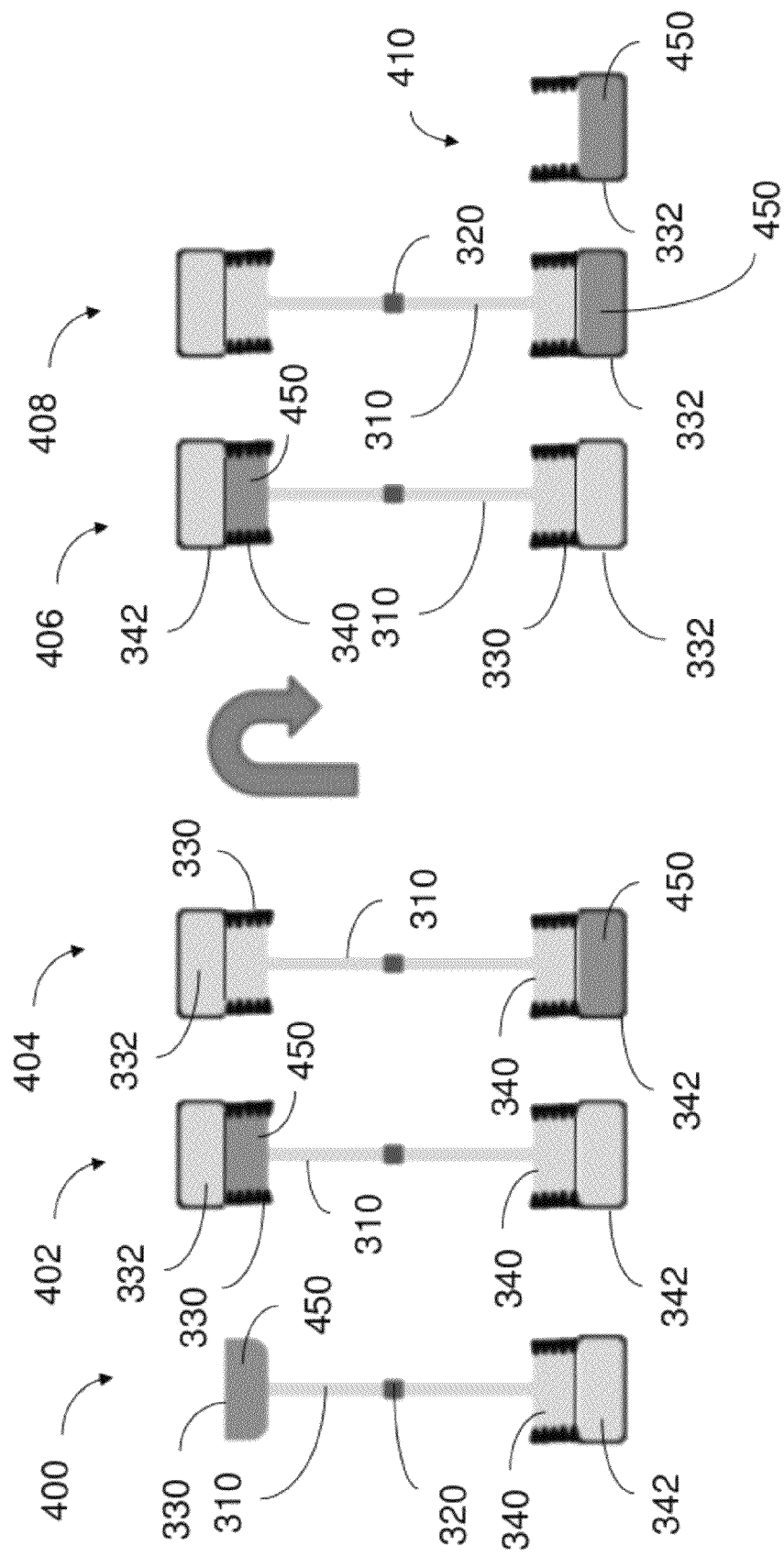
FIG. 20B shows a process for fragmenting nucleic acids using the processing device of FIG. 20A in accordance with an illustrative embodiment.

FIGS. 19-20B depict an illustrative embodiment of a processing device 300. Device 300 includes a channel 310, a shearing orifice 320, a first chamber 330, a first cap 332, a second chamber 340 and a second cap 342. Each of the components described for processing device 300 are in fluid communication. That is, a fluid may flow from the first cap 332 into the first chamber 330, through the channel 310, through shearing orifice 320, into second chamber 340, into second cap 342, and back. First and second caps 332 and 342 can be attached to first and second chambers 330 and 340 by any suitable method. In some embodiments, caps 332 and 342 are attached to chambers 330 and 340 by a screw fit arrangement. In other embodiments, caps 332 and 342 are coupled to chambers 330 and 340 by an adhesive, snap fit or interference fit.

FIG. 19 shows a perspective view of processing device 300 without a depiction of caps 332 and 342. FIG. 20A illustrates processing device 300 with and without caps 332 and 342 attached to respective chambers 330 and 340 to form an air tight seal. In some embodiments, caps 332 and 342 are large enough to hold the entire volume of a sample that is introduced into the processing device 300. It should be understood that it is not necessary for processing device 300 to have two caps on either end. Indeed, for some embodiments, a processing device 300 includes only a first cap for the first chamber while the second chamber has a cover permanently attached or molded thereon. Processing device 300 may be suitably coupled to a flow actuator such as a centrifuge or pump for causing flow of sample material between chambers 330, 340 through the channel 310 and shearing orifice 320. In some embodiments, processing device 300 may be directly placed in a receiving area of a centrifuge for processing of the sample. Or, processing device 300 may be coupled to a holder having an outer structure that is suitably shaped to be placed into a receiving area of a centrifuge, similar to that described above regarding inner portion 10 and outer portion 100. Accordingly, the combination of the processing device and holder may be subject together to forces applied by the centrifuge.

FIG. 20B illustrates a series of steps 400-410 through which a sample 450 containing nucleic acids may be processed. In step 400, sample 450 is loaded into first chamber 330. In some cases, sample 450 does not readily flow into channel 310 due to the combination of viscosity of the sample and the small entrance diameter of the channel. In step 402, cap 332 is attached to chamber 330 to form an air tight seal. Step 404 illustrates the processing device having been subject to forces generated, for example, by a centrifuge. Accordingly, sample 450 flows from the first chamber 330 through the channel 310, through the shearing orifice 320 disposed in the middle of the channel, and into second cap 342. In some embodiments, second cap 342 serves as a collection region for the sample material. It should be appreciated from step 404 that nucleic acids contained in the sample are fragmented due to shear forces from flow of the sample through shearing orifice 320.

Once the sample 450 is collected in the cap 342, the device is subsequently placed in an inverted position, shown in step 406. Once inverted, by gravity, the sample 450 moves into second chamber 340, however, sample 450 does not readily flow into channel 310 due to the viscosity of the sample and the small entrance diameter of the channel. In step 408, the processing device is subject to forces arising, for example, from a centrifuge, causing the sample 450 to flow from the second chamber 340 through the channel 310, through the shearing orifice 320, and into first cap 332. In some embodiments, first cap 332 may also serve as a collection region for the sample material. Accordingly, nucleic acids contained in the sample are once again fragmented due to shear forces from flow of the sample through shearing orifice 320. In step 410, the first cap 332 is removed from the processing device 300 with sample 450 having been processed and fully recovered.

The above process, particularly steps 404-408, can be repeated as many times as desired until a target nucleic acid size distribution is reached. Thus, after step 408, the device can be inverted once again to its original position and subjected to forces applied by a suitable flow actuator (e.g., a centrifuge). Accordingly, the sample 450 would flow back from the first chamber 330 through the channel 310, through the shearing orifice 320, and into second cap 342. Indeed, for some embodiments, device 300 can be inverted and processed however many times as necessary to reach a desired fragmented nucleic acid size range and distribution.

Figure 21A:
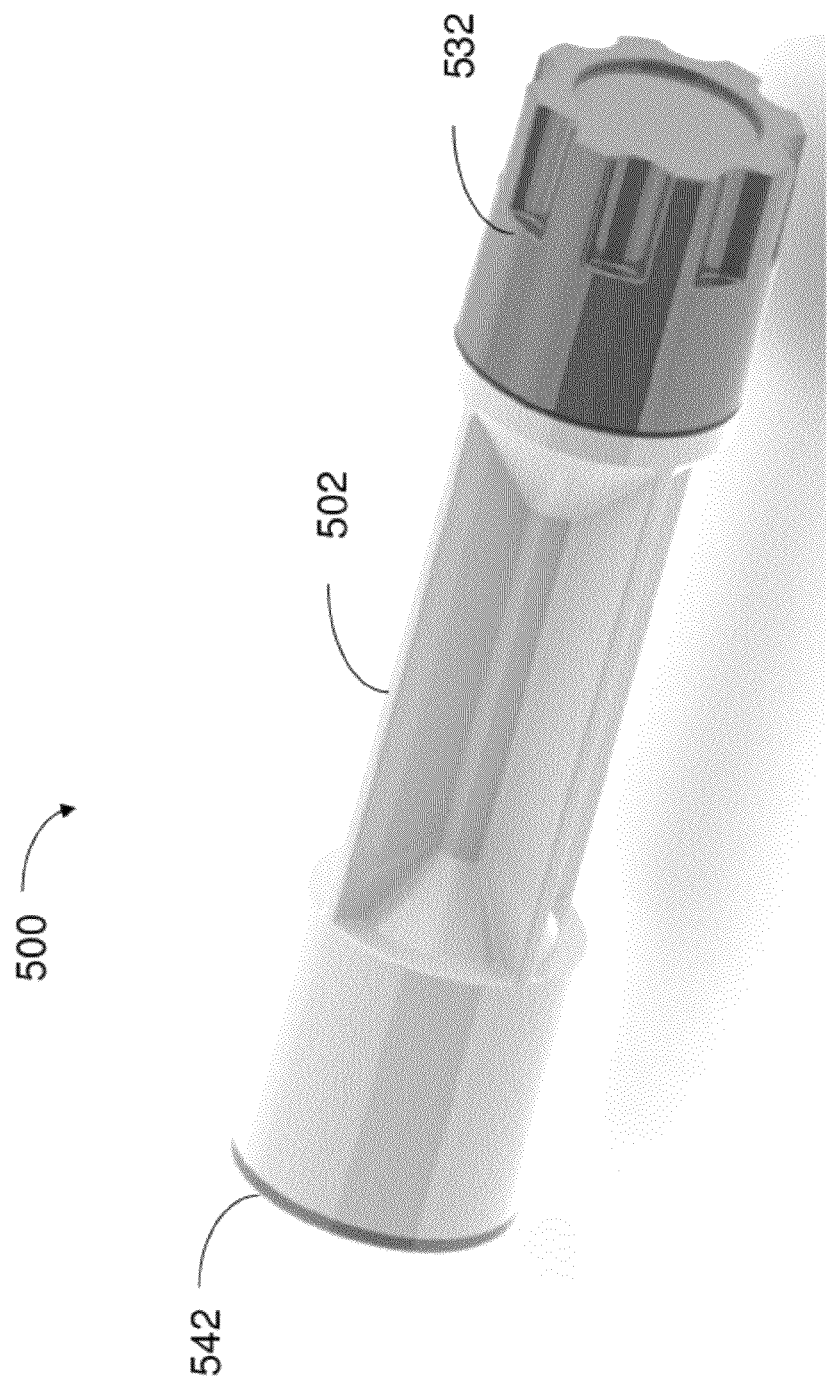
FIG. 21A illustrates a perspective view of a processing device for fragmenting nucleic acids in accordance with an embodiment.

FIG. 21A illustrates a perspective view of another embodiment of a processing device 500 which includes a body 502, first cap 532 and second cap 542. The first cap 532 is twisted on to the body at one end of the body via a screw arrangement and the second cap 542 is adhered to the body at the other end of the device through an interference fit. It can be appreciated that other attachment arrangements are possible. First and second caps 532, 542 are attached at opposite ends of the device to enclose respective chambers 530, 540, and forming an air tight seal. The device also includes first channel 510 disposed between the first chamber 530 and the shearing region 520, and second channel 512 disposed between the shearing region 520 and the second chamber 540. In the embodiment depicted, the inner width of the first channel 510 is less than the inner width of the second channel 512. Other combinations of structure and dimension for the device are possible.

In some embodiments, chambers 530, 540 are large enough to hold the entire volume of a sample that is introduced into the processing device 500. As discussed above, having two caps on either end of suitable processing devices in accordance with embodiments described herein is not required. It can be appreciated that processing devices in accordance with the invention may have caps that can be attached to the main body of the processing in any suitable manner. Further, other suitable caps or arrangements may or may not be used for various processing devices in accordance with inventive features described.

Figure 21B:
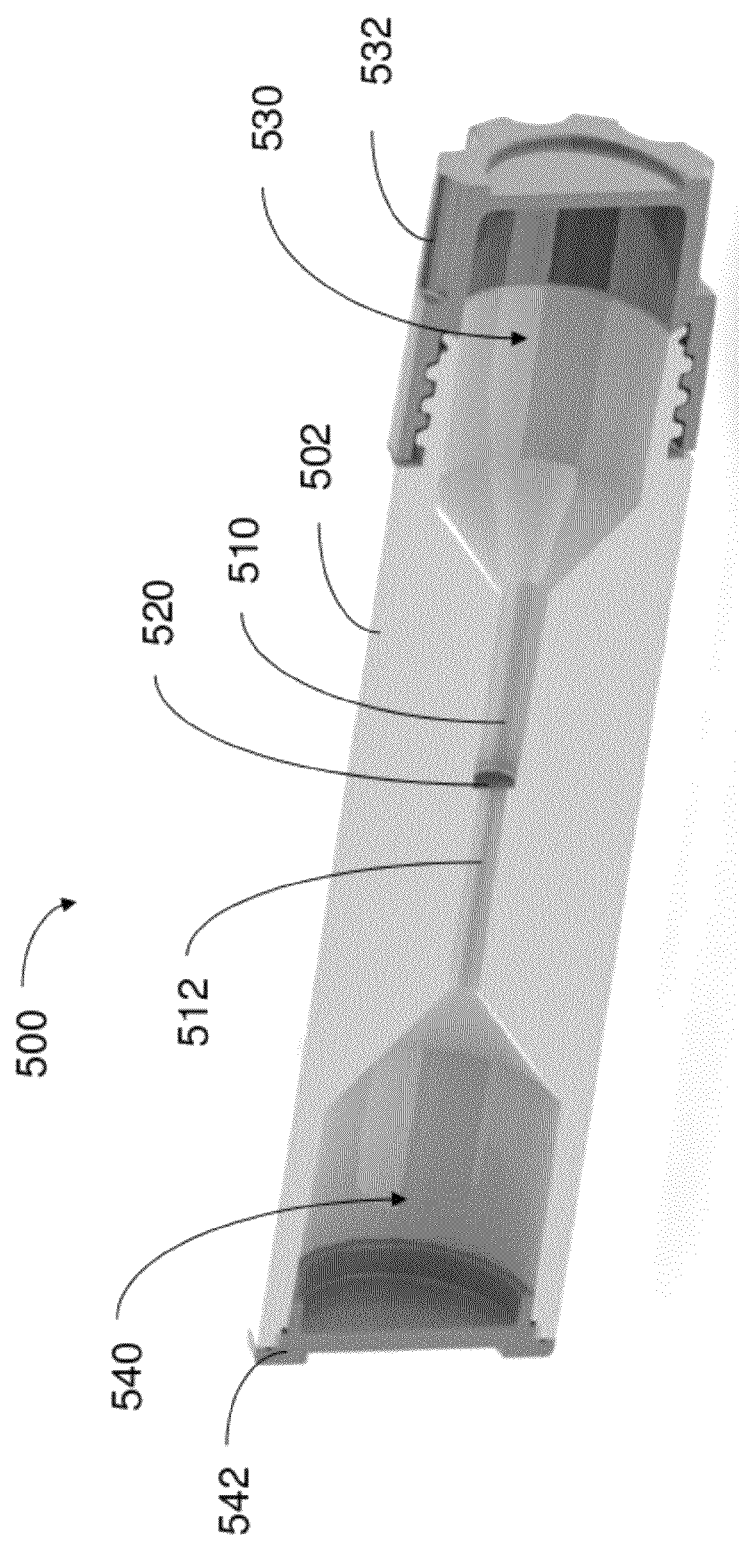
FIG. 21B depicts section view of the processing device of FIG. 21A.

In the embodiment shown in FIG. 21B, sample material having nucleic acids may be caused to flow past the shearing region 520 of the processing device 500 once or multiple times. When in use, the first cap 532 is initially not screwed onto the region of the body 502 at the first chamber 530; whereas the second cap 542 is attached to the body via an interference fit at the second chamber 540. Sample material is introduced into the device at the opening provided at the first chamber 530. Once a sufficient amount of sample material is contained within the device, the first cap 532 is then screwed on tightly to the body of the device, enclosing the sample material within. The device is then subject to force produced by an actuator (e.g., centrifuge, pump, agitation, etc.) causing the sample material to move through the shearing region 520 via the channel 510 and into the second chamber 540 via channel 512. Force may then be applied to the device so as to cause migration of the sample material back through the shearing region 520 via the channels 510, 512 and into the first chamber 530. As shown in the embodiment depicted in FIG. 21B, the cross-sectional area of the channel 510 is greater than the cross-sectional area of the channel 512. In some embodiments, the device 500 is appropriately inverted and the sample is subject to forces so as to move in the reverse direction back toward the first chamber entrance area. The sample may be collected at the cap of the first chamber or may be subject to repeated movement back through the shearing region. Accordingly, the sample material may be subject to shear forces as many times as desired from suitable movement through the shearing region.

EXAMPLES

Example 1

Figure 22:
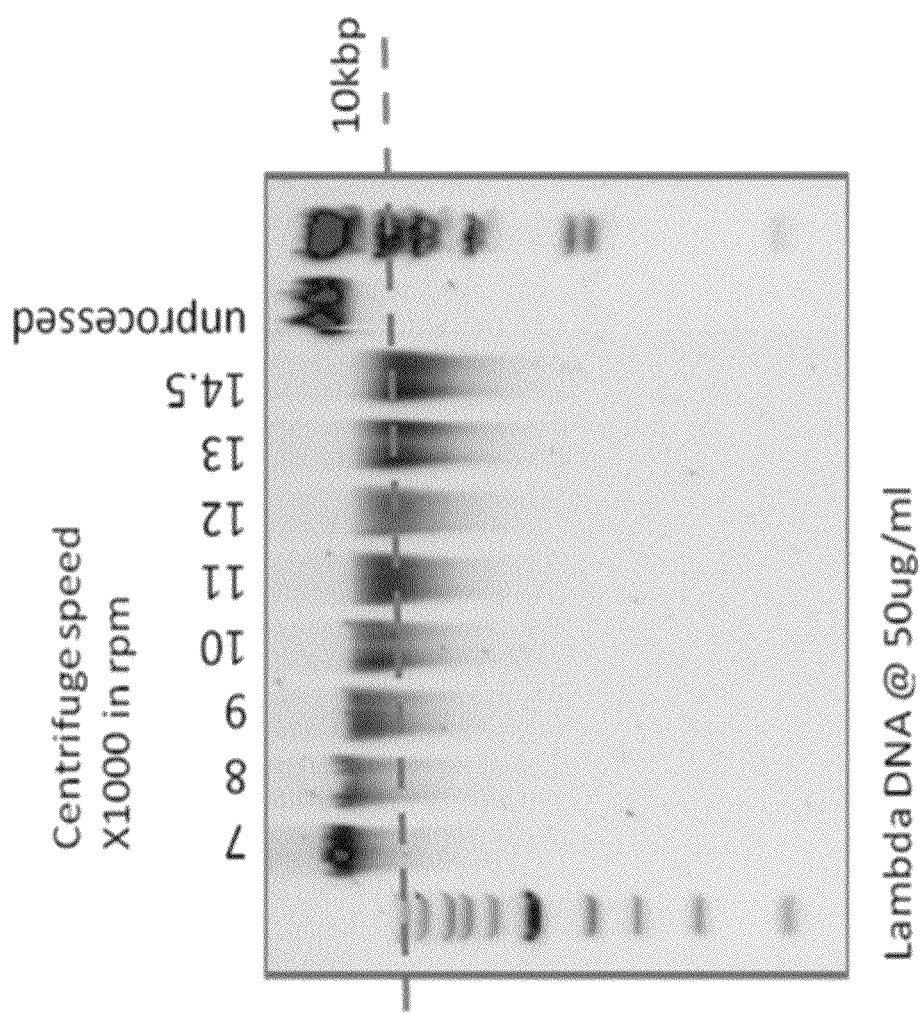
FIG. 22 depicts results from a processing example that tests the effects of varying centrifuge speed in accordance with an embodiment.

A pipette tube for use as an inlet was fitted with a channel and a shearing orifice and placed within a microcentrifuge tube to form a processing device according to embodiments described above. A sample of Lambda DNA having a starting nucleic acid size of 48 kbp at a concentration of 50 micrograms/milliliter was introduced into the pipette tube of the processing device. The device was inserted into a centrifuge and the centrifuge was then operated at varying speeds of 7,000 rpm; 8,000 rpm; 9,000 rpm; 10,000 rpm, 11,000 rpm; 12,000 rpm; 13,000 rpm; and 14,500 rpm. As shown in FIG. 22, the results of the fragmented DNA were compared with the unprocessed sample DNA according to gel electrophoresis analysis. It was observed that operating the centrifuge at speeds of between about 11,000 rpm and about 14,500 rpm for this DNA sample gave rise to DNA having an average nucleic acid size of about 10 kbp. It was also observed that operating the centrifuge at higher speeds for this processing device led to increased DNA fragmentation.

Example 2

Figure 23:
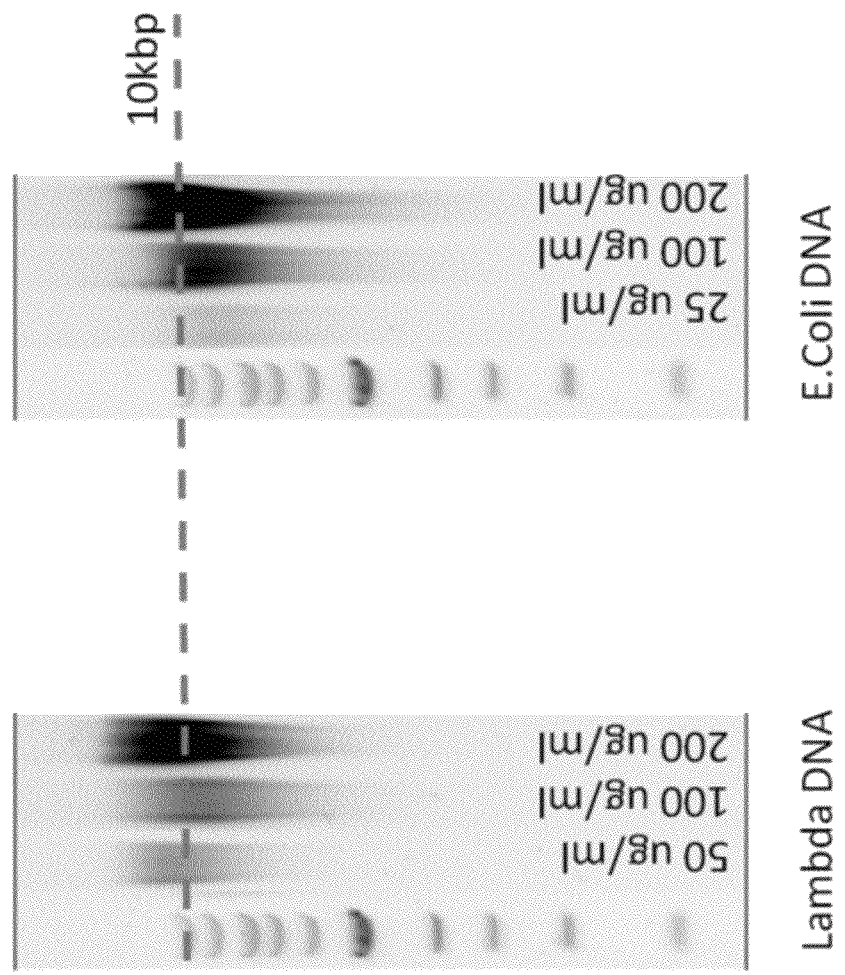
FIG. 23 shows results from a processing example that tests differences in varying the concentration of a sample in accordance with an embodiment.

Using the same processing device as that described in Example 1, 200 microliters of Lambda DNA and E. Coli DNA at varying concentrations were processed using a centrifuge operating at 13,000 rpm. The concentrations of Lambda DNA were 50 micrograms/milliliter, 100 micrograms/milliliter, and 200 micrograms/milliliter. The concentrations of E. Coli DNA were 25 micrograms/milliliter, 100 micrograms/milliliter, and 200 micrograms/milliliter. As shown in FIG. 23, the fragmented DNA from the Lambda and E. Coli samples after processing resulted in average nucleic acid sizes of about 10 kbp.

Example 3

Four processing devices similar to that described in Example 1 were created, yet, with shearing orifices having different diameters; that is, the diameters were 10 microns, 20 microns, 30 microns and 50 microns. The processing devices were filled with Lambda DNA and placed in a centrifuge which was then operated at 10,000 rpm and 14,000 rpm. At 10,000 rpm, the average nucleic acid sizes for the 20 micron and 30 micron diameter shearing orifices upon processing was about 6.4 kbp and about 7.0 kbp, respectively. At 14,000 rpm, the average nucleic acid sizes for the 10 micron, 20 micron, 30 micron and 50 micron diameter shearing orifices after processing was about 5.2 kbp, about 5.2 kbp, about 6.0 kbp and about 9.0 kbp, respectively. It was observed that using smaller diameter shearing orifices for this processing device led to increased DNA fragmentation. It was also observed that operating the centrifuge at higher speed also resulted in an increased amount of DNA fragmentation.

Example 4

Figure 24:
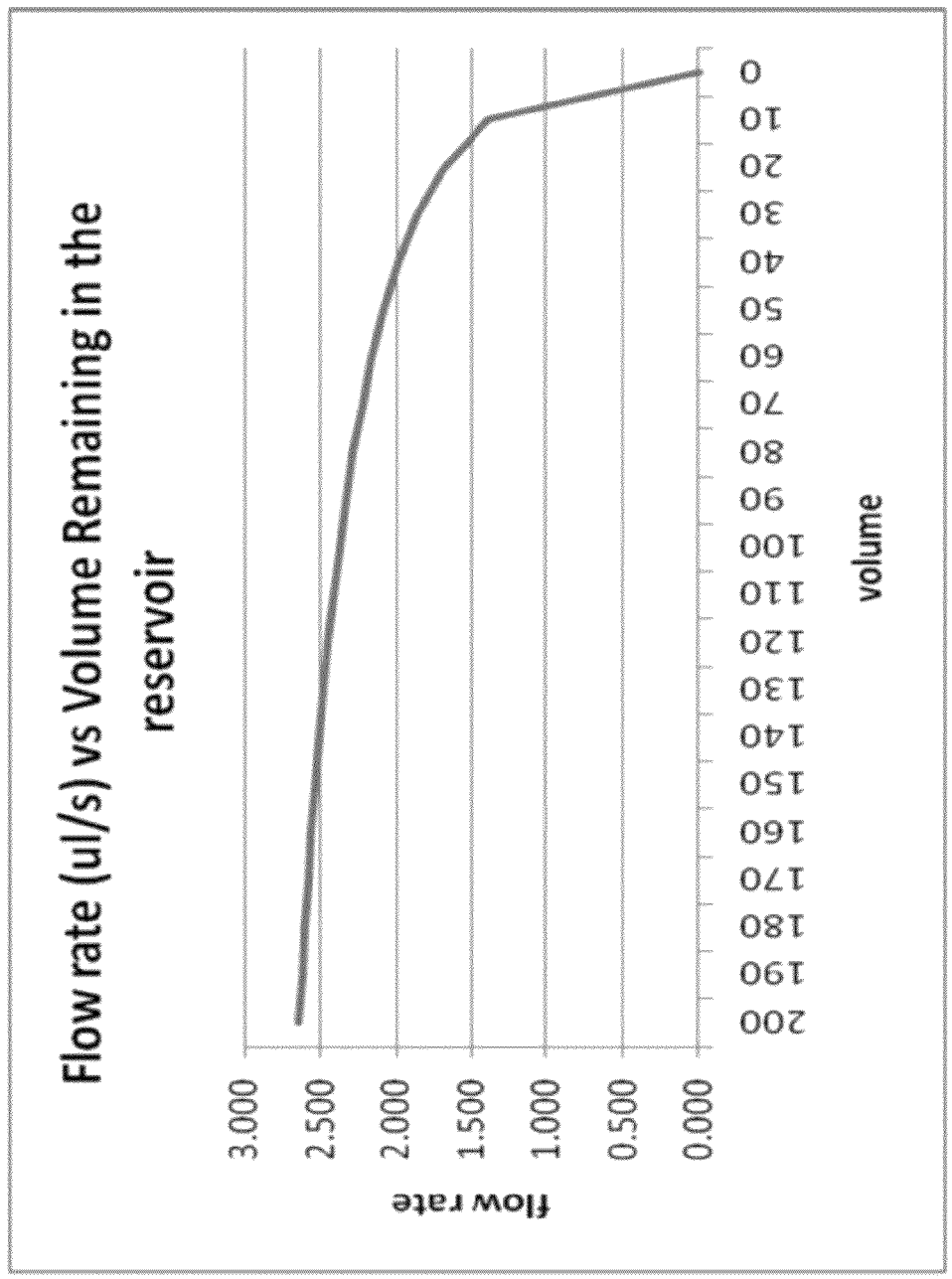
FIG. 24 depicts results from a processing example that illustrates the variation of flow rate through a device as the sample volume remaining in a portion of the device changes in accordance with an embodiment.
Figure 25:
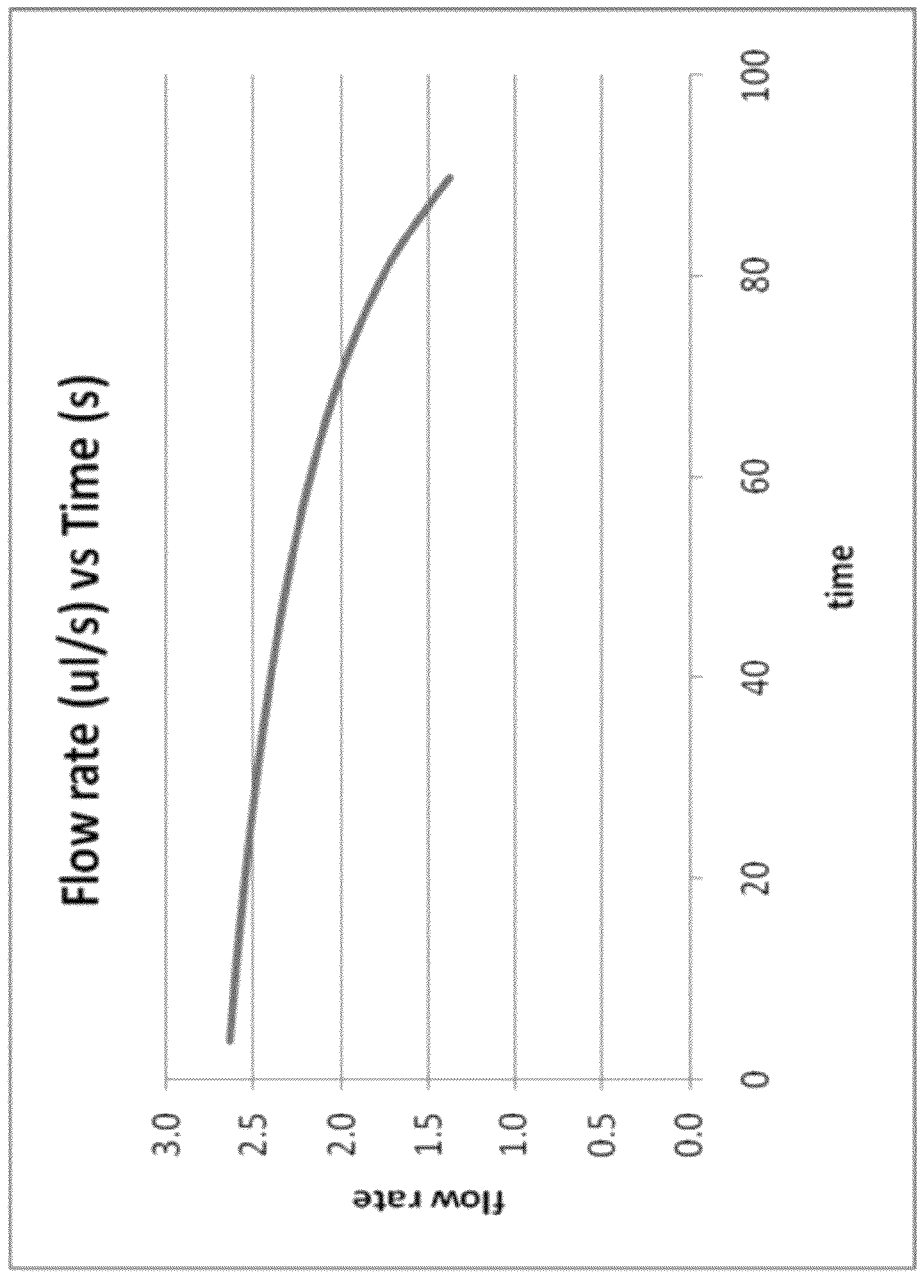
FIG. 25 shows results from the processing example of FIG. 24 that illustrates the change in flow rate with processing time.

Using the processing device of Example 3 having shearing with a 10 micron diameter, the flow rate of a liquid sample was measured during processing at a steady centrifuge rate of 12,000 rpm. As shown in FIGS. 24 and 25, the flow rate through the processing device experiences a slight decrease during most of the fragmenting process, generally considered to be a relatively constant flow rate. Although the flow rate decreased significantly when less than 10 microliters of liquid sample was left in the inlet reservoir, for volumes of liquid sample above 10 microliters, the flow rate was generally consistent, ranging between about 1.0 microliters/second and about 3.0 microliters/second.

Example 5

Processing devices having two shearing orifices according to embodiments described in FIGS. 17 and 18 were used with different radial distances and sample heights between the shearing orifices. Shearing orifices having diameters of 50 microns, 40 microns, 35 microns and 30 microns were also evaluated. The Table below describes maximum flow rates corresponding to shearing orifices positioned at two different locations in the processing device, along with respective diameters of shearing orifices. As the position of a shearing orifice varies, the radial distance from the rotational axis of the centrifuge will change, affecting the flow rate through the shearing orifices. In addition, the flow rate through a shearing orifice was generally observed to be faster as the diameter of the orifice was larger.

|  | Radial Distance from Rotational Axis | Sample height above shearing orifice | 50 micron inner diameter | 40 micron inner diameter | 35 micron inner diameter | 30 micron inner diameter |
| --- | --- | --- | --- | --- | --- | --- |
| First Shearing Orifice | 33 mm | 10 mm | 40 μL/sec | 25 μL/sec | 19 μL/sec | 14 μL/sec |
| Second Shearing Orifice | 43 mm | 10 mm | 46 μL/sec | 30 μL/sec |  | 17 μL/sec |

Figure 26:
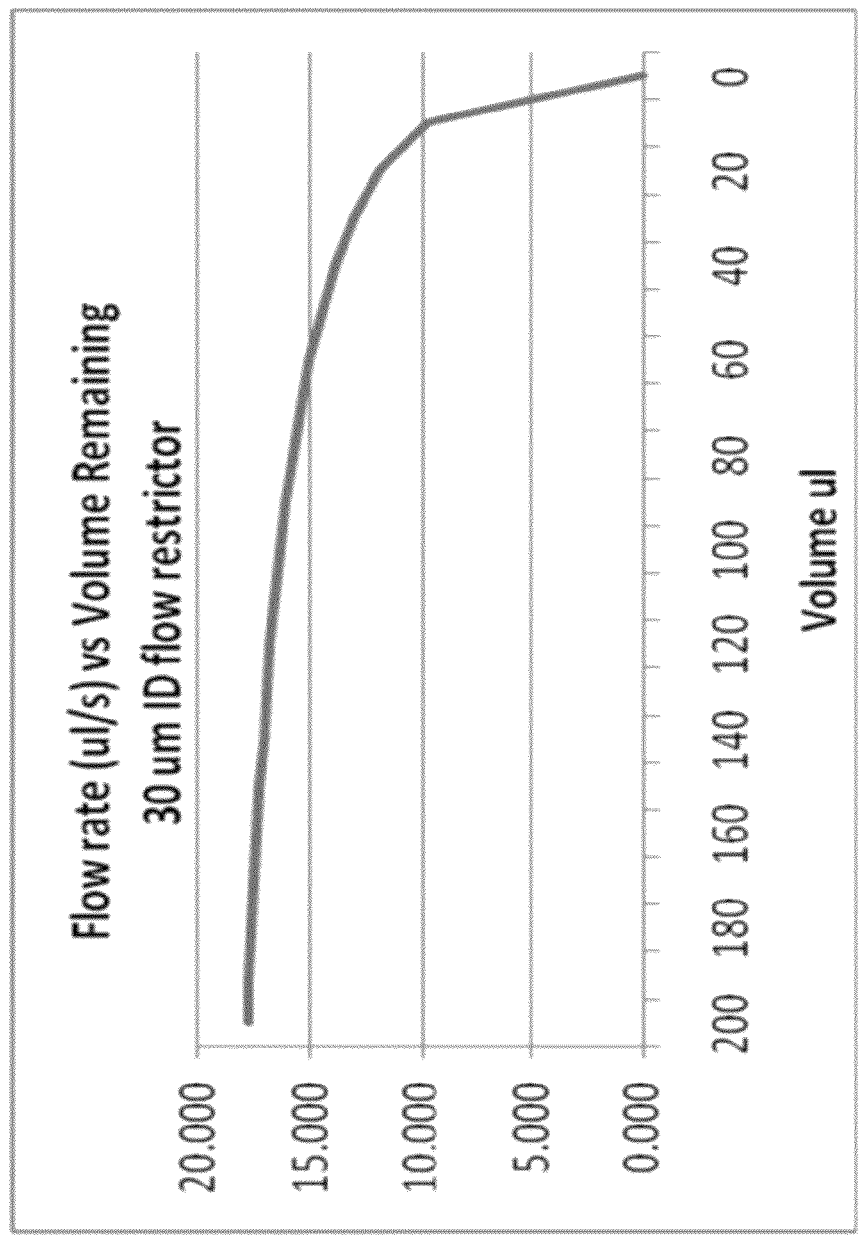
FIG. 26 illustrates results from another processing example that shows the change in flow rate through a device as the sample volume remaining in a portion of the device changes in accordance with an embodiment.

As shown in FIG. 26, the flow rate remains generally constant throughout the DNA fragmentation process. The flow rate decreased significantly when less than 10 microliters of liquid sample was left in the inlet reservoir, however, for volumes of liquid sample above 10 microliters, the flow rate was relatively constant, ranging between about 10.0 microliters/second and about 20.0 microliters/second.

Example 6

A processing device according to the embodiments described in FIGS. 19-20B was manufactured. That is, the device is able to be processed in a first position, and subsequently in a second position where the device is inverted so that the bottom side faces up and the top side faces down. MG DNA and Lambda DNA were processed once, twice, and four times, where the device was inverted in orientation upon each successive processing step. That is, the device was inverted in orientation three times when processed four times; the device was inverted once when processed two times; and the device was not inverted in orientation when processed once. In addition, the centrifuge was operated at 7,000 rpm during each processing step. As shown in FIG. 27, it was observed that processing the samples containing MG DNA and Lambda DNA four times yielded a tight distribution where average nucleic acid sizes were about 10 kbp.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. It will be apparent that other embodiments and various modifications may be made to the present invention without departing from the scope thereof. The foregoing description of the invention is intended merely to be illustrative and not restrictive thereof. The scope of the present invention is defined by the appended claims and equivalents thereto.

The invention claimed is:

1. A processing device for fragmenting nucleic acids contained within a sample, the device comprising:
   a first chamber for receiving the sample containing nucleic acids;
   a first cap attached to the first chamber;
   a channel in fluid communication with the first chamber, the channel having a volume;
   a shearing orifice in fluid communication with the channel and adapted to fragment the nucleic acids in the sample upon flow of the sample through the shearing orifice, wherein the first chamber and the channel are constructed and arranged to maintain a relatively constant pressure at an entrance of the shearing orifice during flow of a majority of a sample through the shearing orifice, the sample having a sample volume that is at least 2 times the channel volume;
   a second chamber in fluid communication with the shearing orifice and for receiving the sample containing the fragmented nucleic acids from the shearing orifice, wherein the first chamber, the channel, the shearing orifice and the second chamber are constructed and arranged for use with a flow actuator to move the sample containing nucleic acids from the first chamber through the channel and the shearing orifice into the second chamber, wherein only one shearing orifice is located between the first chamber and the second chamber; and
   a second cap attached to the second chamber.

2. The device of claim 1, wherein the shearing orifice is adapted to cause fragmentation of nucleic acids in the sample from an average nucleic acid size of between 40 kbp and 1 Gbp to an average nucleic acid size of between about 5 kbp and about 20 kbp upon flow of the sample through the shearing orifice.

3. The device of claim 1, wherein the first chamber and the channel are constructed and arranged to maintain pressure at the entrance of the shearing orifice to within about 40% less of an initial pressure during flow of a majority of the sample through the shearing orifice.

4. The device of claim 1, wherein the channel has a length of between about 5 mm and about 20 mm.

5. The device of claim 1, wherein the first chamber and channel are constructed and arranged to maintain a sample height that is approximately constant during flow of a majority of the sample through the shearing orifice.

6. The device of claim 1, wherein the first chamber and the channel are constructed and arranged to maintain a relatively constant volume flow rate at an entrance of the shearing orifice during flow of a majority of the sample through the shearing orifice.

7. The device of claim 6, wherein the first chamber and the channel are constructed and arranged to maintain a volume flow rate at an entrance of the shearing orifice to within about 50% of an initial volume flow rate during flow of a majority of the sample through the shearing orifice.

8. The device of claim 1, wherein a cross-sectional area of the first chamber is five times or more than a cross-sectional area of the channel.

9. The device of claim 1, wherein the first chamber and the channel are constructed and arranged to maintain a relatively constant pressure at an entrance of the shearing orifice during flow of a majority of a sample through the shearing for a sample having a sample volume that is at least 5 times the channel volume.

10. The device of claim 1, wherein the first chamber and the channel are constructed and arranged such that a velocity of sample flow through the shearing orifice is greater than a velocity of sample flow within the first chamber during flow of sample through the shearing orifice.

11. The device of claim 1, wherein the shearing orifice comprises an entrance portion having a wall that forms an angle perpendicular to a direction of flow of the sample through the shearing orifice.

12. The device of claim 1, wherein the flow actuator comprises a centrifuge.

13. The device of claim 1, wherein the first chamber, the channel, the shearing orifice and the second chamber are constructed and arranged for use in the centrifuge in either a first orientation or in a second orientation that is inverted with respect to the first orientation.

14. The device of claim 1, wherein the shearing orifice is constructed and arranged to cause cells contained within the sample to lyse when the sample flows through the shearing orifice.

15. The device of claim 1, wherein a portion of the shearing orifice that contacts the sample is made of a material including at least one of glass, sapphire, ruby, metal, or ceramic.

16. The device of claim 1, wherein the shearing orifice has a width of between about 10 microns and about 100 microns, and a length of between about 100 microns and about 20 mm.

17. The device of claim 1, wherein the first chamber includes a funnel shaped reservoir for receiving the sample containing nucleic acids.

18. A processing device for fragmenting nucleic acids contained within a sample, the device comprising:
an inlet for receiving the sample containing nucleic acids;
a shearing orifice in fluid communication with the inlet and adapted to fragment the nucleic acids in the sample upon flow of the sample through the shearing orifice; and
a collection chamber in fluid communication with the shearing orifice and for receiving the sample containing the fragmented nucleic acids from the shearing orifice, wherein the inlet, the shearing orifice and the collection chamber are constructed and arranged for use with a centrifuge in a first orientation within a receptacle of the centrifuge to accommodate flow of the sample from the inlet through the shearing orifice and into the collection chamber, and for use in a second orientation that is inverted with respect to the first orientation within the receptacle of the centrifuge to accommodate flow of the sample from the collection chamber back through the shearing orifice and into the inlet.

19. The device of claim 18, wherein the shearing orifice is adapted to cause fragmentation of nucleic acids in the sample from an average nucleic acid size of between 40 kbp and 1 Gbp to an average nucleic acid size of between about 5 kbp and about 20 kbp upon flow of the sample through the shearing orifice.

20. The device of claim 18, wherein the first orientation includes a first end facing in a direction away from a center of rotation in a centrifuge and a second end facing in a direction toward a center of rotation in the centrifuge, and the second orientation includes the second end facing in the direction away from a center of rotation in the centrifuge and the first end facing in the direction toward a center of rotation in the centrifuge.

21. The device of claim 18, wherein the collection chamber comprises a cap for receiving the sample containing the fragmented nucleic acids from the shearing orifice.

22. The device of claim 18, wherein the inlet includes a funnel shaped reservoir for receiving the sample containing nucleic acids.

23. The device of claim 18, wherein the shearing orifice is constructed and arranged to cause cells contained within the sample to lyse when the sample flows through the shearing orifice.

24. The device of claim 18, wherein a portion of the shearing orifice that contacts the sample is made of a material comprising at least one of glass, sapphire, ruby, metal, or ceramic.

25. The device of claim 18, wherein the shearing orifice comprises an orifice having a width of between about 10 microns and about 100 microns, and a length of between about 100 microns and about 20 mm.

26. The device of claim 18, further comprising a channel in fluid communication with the inlet and the shearing orifice, wherein the inlet and the channel are constructed and arranged to maintain a relatively constant pressure at an entrance of the shearing orifice during flow of a majority of the sample through the shearing orifice.

27. The device of claim 26, wherein the inlet and the channel are constructed and arranged to maintain a sample height that is constant during flow of a majority of the sample through the shearing orifice.

28. The device of claim 26, wherein the channel has a length of between about 5 mm and about 20 mm.

29. The device of claim 26, wherein the inlet and the channel are constructed and arranged to maintain a relatively constant volume flow rate at an entrance of the shearing orifice during flow of a majority of the sample through the shearing orifice.

30. The device of claim 18, wherein the inlet and the channel are constructed and arranged such that a velocity of sample flow through the shearing orifice is greater than a velocity of sample flow within the inlet during flow of sample through the shearing orifice.

31. A processing device for fragmenting nucleic acids contained within a sample, the device comprising:
an inlet for receiving the sample containing nucleic acids;
a channel in fluid communication with the inlet, the channel having a volume;
a plurality of shearing orifices disposed in a series arrangement in fluid communication with the channel and adapted to fragment the nucleic acids in the sample upon flow of the sample through the plurality of shearing orifices, wherein the inlet and the channel are constructed and arranged to maintain a relatively constant pressure at an entrance of the plurality of shearing orifices during flow of a majority of a sample through the plurality of shearing orifices, the sample having a sample volume that is at least 2 times the channel volume, and wherein the plurality of shearing orifices includes a first orifice and a second orifice, the first orifice having a cross sectional area larger than the second orifice; and a collection chamber in fluid communication with the plurality of shearing orifices and for receiving the sample containing the fragmented nucleic acids from the plurality of shearing orifices, wherein the inlet, the channel, the plurality of shearing orifices and the collection chamber are constructed and arranged for use with a flow actuator to move the sample containing nucleic acids from the inlet through the channel and the plurality of shearing orifices into the collection chamber.

* * * * *